United States Patent
Novak et al.

(10) Patent No.: US 11,229,910 B2
(45) Date of Patent: Jan. 25, 2022

(54) MICROFLUIDIC DEVICES AND SYSTEMS FOR CELL CULTURE AND/OR ASSAY

(71) Applicants: President and Fellows of Harvard College, Cambridge, MA (US); Tufts University, Boston, MA (US)

(72) Inventors: Richard Novak, Boston, MA (US); Donald E. Ingber, Boston, MA (US); Michael Levin, Beverly, MA (US); Rachelle Prantil-Baun, Ashland, MA (US)

(73) Assignees: President and Fellows of Harvard College, Cambridge, MA (US); Tufts University, Boston, MA (US)

( * ) Notice: Subject to any disclaimer, the term of this patent is extended or adjusted under 35 U.S.C. 154(b) by 744 days.

(21) Appl. No.: 15/752,547

(22) PCT Filed: Aug. 12, 2016

(86) PCT No.: PCT/US2016/046880
§ 371 (c)(1),
(2) Date: Feb. 13, 2018

(87) PCT Pub. No.: WO2017/027838
PCT Pub. Date: Feb. 16, 2017

(65) Prior Publication Data
US 2019/0009274 A1    Jan. 10, 2019

Related U.S. Application Data

(60) Provisional application No. 62/204,756, filed on Aug. 13, 2015, provisional application No. 62/263,970, filed on Dec. 7, 2015.

(51) Int. Cl.
*B01L 3/00* (2006.01)
*G01N 33/50* (2006.01)
(Continued)

(52) U.S. Cl.
CPC ....... *B01L 3/502761* (2013.01); *C12M 23/16* (2013.01); *C12N 5/0068* (2013.01);
(Continued)

(58) Field of Classification Search
CPC ....... B01L 3/502761; B01L 2200/0668; B01L 2300/0645; B01L 2300/0816;
(Continued)

(56) References Cited

U.S. PATENT DOCUMENTS 5,135,875 A   8/1992 Hoess
6,767,706 B2  7/2004 Quake
(Continued)

FOREIGN PATENT DOCUMENTS

EP        0 471 293 A2    2/1992
WO    WO 2012/154729 A1  11/2012
(Continued)

OTHER PUBLICATIONS

Balaconis, M.K. et al., "Biodegradable optode-based nanosensors for in vivo monitoring," Anal. Chem. 84(13), Jul. 3, 2012, pp. 5787-5793 (13 pages).
(Continued)

*Primary Examiner* — William H. Beisner
*Assistant Examiner* — Danielle B Henkel
(74) *Attorney, Agent, or Firm* — Nixon Peabody LLP

(57) ABSTRACT

Described herein are microfluidic devices and systems for high density cell culture and/or high throughput cell assays. Methods of using the same are also provided herein. In some embodiments, the microfluidic devices and systems described herein provide rapid and automated trapping of single embryos in ordered arrays.

16 Claims, 8 Drawing Sheets

(51) Int. Cl.

| | |
|---|---|
| *G01N 21/64* | (2006.01) |
| *G01N 35/00* | (2006.01) |
| *C12N 5/00* | (2006.01) |
| *C12M 3/06* | (2006.01) |
| *G01N 35/10* | (2006.01) |

(52) U.S. Cl.
CPC ..... *G01N 21/6458* (2013.01); *G01N 33/5088* (2013.01); *G01N 35/00029* (2013.01); *B01L 2200/0668* (2013.01); *B01L 2300/0645* (2013.01); *B01L 2300/0816* (2013.01); *B01L 2300/0864* (2013.01); *B01L 2300/0883* (2013.01); *G01N 35/1081* (2013.01); *G01N 2021/6482* (2013.01); *G01N 2035/00158* (2013.01); *G01N 2035/00237* (2013.01)

(58) Field of Classification Search
CPC .... B01L 2300/0864; B01L 2300/0883; C12M 23/16; C12N 5/0068; G01N 21/6458; G01N 33/5088; G01N 35/00029; G01N 35/1081; G01N 2021/6482; G01N 2035/00158; G01N 2035/00237

See application file for complete search history.

(56) References Cited

U.S. PATENT DOCUMENTS

| | | | |
|---|---|---|---|
| 7,993,851 | B2 | 8/2011 | Holets-McCormack |
| 10,087,408 | B2 * | 10/2018 | Hansen .................. C12M 23/16 |
| 2003/0138941 | A1 * | 7/2003 | Gong .................... B01L 3/5027 435/287.2 |
| 2004/0229349 | A1 * | 11/2004 | Daridon ................ C12M 21/06 435/305.2 |
| 2007/0074972 | A1 * | 4/2007 | Nassef ................ F16K 99/0015 204/451 |
| 2008/0020401 | A1 | 1/2008 | Grenier |
| 2011/0143964 | A1 * | 6/2011 | Zhou ..................... B01L 3/5027 506/26 |
| 2011/0262906 | A1 * | 10/2011 | Dimov ............. B01L 3/502761 435/6.1 |
| 2011/0294140 | A1 | 12/2011 | Holets-McCormack |
| 2012/0091235 | A1 | 4/2012 | Li |
| 2012/0288875 | A1 | 11/2012 | Grenier |
| 2013/0190212 | A1 * | 7/2013 | Handique .............. B01L 3/021 506/37 |
| 2014/0248621 | A1 | 9/2014 | Collins |
| 2015/0343444 | A1 | 12/2015 | Manalis |

FOREIGN PATENT DOCUMENTS

| | | |
|---|---|---|
| WO | WO 2014/210339 A1 | 12/2014 |
| WO | WO 2015/002975 A1 | 1/2015 |
| WO | WO 2017/024044 A1 | 2/2017 |

OTHER PUBLICATIONS

Becker, H. et al., "Polymer microfabrication methods for microfluidic analytical applications," Electrophoresis 21(1), Jan. 2000, pp. 12-26 (15 pages).
Becker, H. et al., "Polymer microfluidic devices," Talanta, 56(2), 2002, pp. 267-287 (21 pages).
Beebe D.J. et al., , "Microfluidic tectonics: A comprehensive construciton platform for microfluidic systems," Proc. Natl. Acad. Sci. 97(25), Dec. 5, 2000, pp. 13488-13493 (6 pages).
Fiorini, G.S. et al., "Disposable microfluidic devices: fabrication, function, and applicaiton," BioTechniques 38(3), 2005, pp. 429-446 (18 pages).
Gourley, P.L., "Biocavity laser for high-speed cell and tumour biology," J. Phys. D.: Appl. Phys. 36, 2003, pp. R228-R239 (13 pages).
McDonald, J.C. et al., "Poly(dimethylsiloxane) as a material for fabrication microfluidic devices," Accounts of Chemical Research 35(7), Jul. 2002, pp. 491-499 (9 pages).
Piccin, E. et al., "Polurethane from biosource as a new material for fabrication of microfluidic devices for rapid prototyping," Journal of Chromatography A, 1173, Nov. 2007, pp. 151-158 (8 pages).
Rossier, J.S. et al., "Plasma etched polymer microelectrochemical systems," Lab Chip, 2, 2002, pp. 145-150 (6 pages).
Ruckh, T.R. et al., "Polymer-Free Optode Nanosensors for Dynamic, Reversible, and Ratiometric Sodium Imaging in the Physiological Range," Sci. Rep., 3:3366, 2013, pp. 1-6 (6 pages).
Toh, A.G.G. et al., "Engineering microfluidic concentration gradient generators for biological applications," Microfluidics and Nanofluidics, 16 (1-2), 2014, pp. 1-18 (30 pages).
Wallemacq, P.E. et al., "Evaluation of the New AxSYM Cyclosporine Assay: Comparison with TDx Monoclonal Whole Blood and EMIT Cyclosporine Assays," Clin. Chem., 45(3), Mar. 1999, pp. 432-435 (4 pages).
Yatscoff, R.W. et al., "Abbott TDx Monoclonal Antibody Assay Evaluated for Measuring Cyclosporine in Whole Blood," Clin. Chem. 36(11), 1990, pp. 1969-1973 (5 pages).
Zhu, F. et al., "Fishing on Chips: Up-and-Coming Technological Advances in Analysis of Zebrafish and *Xenopus* Embryos," Cytometry Part A, 85(A), Nov. 2014, pp. 921-932 (12 pages).
International Search Report in International Application No. PCT/US16/46880, dated Oct. 21, 2016 (3 pages).
Written Opinion in International Application No. PCT/US16/46880, dated Oct. 21, 2016 (7 pages).

* cited by examiner

MICROFLUIDIC DEVICES AND SYSTEMS FOR CELL CULTURE AND/OR ASSAY

CROSS-REFERENCE TO RELATED APPLICATIONS

This application is a national stage of International Application No. PCT/US2016/046880, filed on Aug. 12, 2016, which claims priority to and benefit of U.S. Provisional Patent Application Ser. No. 62/204,756, filed on Aug. 13, 2015, and U.S. Provisional Patent Application Ser. No. 62/263,970, filed on Dec. 7, 2015, each of which is hereby incorporated by reference herein in its entirety.

FIELD OF THE INVENTION

Various aspects provided herein relate to microfluidic devices and systems for cell culture and/or cell assays. In particular embodiments, the microfluidic devices and systems can be used for high-density cell culture and/or high-throughput cell assays.

BACKGROUND OF THE INVENTION

*Xenopus* offers an attractive model organism for high-throughput organism-level compound screens due to its small size (e.g., ~1.5 mm for size of eggs and up to ~10 mm for size of young tadpoles). This allows for high-density cultures, which are not possible with mice or larger organisms. Furthermore, *Xenopus* is evolutionarily closer to humans, which can provide more accurate data when pursuing human therapies or basic biology. However, one of the biggest challenges for high-throughput *Xenopus* screening includes the complexity of imaging when the embryos are cultured in 48 or 96 well standard plates. Using these standard screen approaches, the embryos can move in the culture medium as a result of plate movement or medium exchange, and they can assume various orientations that can impede imaging where repeatedly monitoring the embryos in the same orientation is needed. Furthermore, plate-based cultures with multiple embryos per well could result in experimental bias: due to the effect of one embryo dying, which can affect the rest of the embryos in the same well. In addition, time-resolved assays are generally difficult to perform in plates, since any secreted molecules diffuse into a larger volume and get diluted out, and/or each stimulation or sampling event requires fluid handling in the form of a robotic fluid handler or extensive manual pipetting. Moreover, the loading of a specific number of embryos per well (e.g., a single embryo per well) requires either sorting or manual pipetting/counting, which limits throughput and is prone to error.

While microfluidic devices for culture and analysis of zebrafish and *Xenopus* embryos have been previously reported (Zhu et al., "Fishing on chips: up-and-coming technological advances in analysis of zebrafish and *Xenopus* embryos" Cytometry Part A (2014) 85A:921-932), there is still a need for development of a microfluidic device or system that is capable of high-throughput trapping and culture of single embryos in individual chambers without cross-talk or cross-communication, e.g., due to embryo death or contamination/exposure to a test agent, as well as high-throughput screening and/or analyzing the embryos.

SUMMARY OF THE INVENTION

Aspects of the present disclosure relate to microfluidic devices and/or systems that allow rapid trapping of single target biological specimens in a high-throughput manner and/or screening of a large number of individual target biological specimens for various cell-based assay applications, including, e.g., but not limited to high-density cell culture, identifying molecular targets, drug screening, and/or identifying rare biological specimens. By way of example only, the devices and/or systems can be used to identify specific specimens of desirable phenotypes (e.g., to identify susceptible, resistant, or tolerant specimens (e.g., embryos)) for further manipulation and/or analysis. Alternatively or additionally, the devices and/or systems can be used to screen a library of drugs (e.g., ion channel drugs) on target biological specimens to identify drugs that confer optimal tolerance.

As an example, the inventors have developed a microfluidic device that can rapidly separate at least about 100-250 embryos into ordered, indexed arrays with embryos geometrically constrained for optimal imaging, and can also allow optical access for automated imaging using various imaging modalities, e.g., brightfield and/or fluorescence modalities. In addition, the microfluidic device is designed such that each target biological specimen (e.g., embryo) receives fresh fluid that has not been contacted by other biological specimens (e.g., embryos). This feature is beneficial to various applications, e.g., in a robust analysis of pathogen response where large numbers of embryos can be susceptible to dying and cross-talk between embryos, e.g., due to an embryo death, could significantly affect the outcome of an assay. Moreover, a fluid pump system (e.g., but not limited to a vacuum driven system) can deliver a fluid (e.g., culture medium) from an on-device reservoir across the target biological specimens (e.g., embryos). In addition, by loading (e.g., in a "plug and play" manner) a plurality of (e.g., at least 2 or more, including, e.g., at least 2, at least 3, at least 4, at least 5, at least 6, at least 7, at least 8, at least 9, at least 10, or more) microfluidic devices as described herein into an automated fluid handling and imaging instrument, a high-throughput system can be developed to enable rapid trapping of at least about 1,200 to about 2000 embryos (e.g., *Xenopus* embryos) per experiment followed by in situ parallel culture (e.g., for a duration of about 3-7 days) and screening of the embryos on-device (e.g., repeated imaging over a period of time) or off-device. In some embodiments, the system can provide full cell and/or embryo culture capabilities, including, e.g., but not limited to medium exchange/perfusion, pH, oxygen, temperature, and/or medium quality logging and maintenance. Accordingly, embodiments of various aspects described herein relate to microfluidic devices and systems for high-throughput cell culture and/or assays as well as uses thereof.

Some aspects described herein relate to microfluidic devices for high-throughput cell culture and/or assay. In one aspect, a microfluidic device comprises (a) a main channel system having an inlet, an outlet, a central portion located between the inlet and the outlet, and a plurality of first chambers, the first chambers extending transversely to a first channel segment within the central portion, each of the first chambers having a channel opening that fluidly communicates with the first channel segment and a medium opening located away from the channel opening, each of the first chambers being sized to receive a single target biological specimen from the first channel segment; and (b) a medium-manifold system having a medium inlet for receiving a culture medium and a plurality of first connecting channels, each of the first connecting channels distributing the culture medium to the corresponding first chamber through the medium opening of the corresponding first chamber. Each of the first connecting channels is configured such that the culture medium exposed to the biological specimen received in the corresponding first chamber does not contact another biological specimen received in another first chamber.

In another aspect, a microfluidic device comprises: (a) a main channel system having an inlet, an outlet, a central portion located between the inlet and the outlet, and a plurality of first chambers, the first chambers extending transversely to a first channel segment within the central portion, each of the first chambers having a channel opening that fluidly communicates with the first channel segment and a medium opening located away from the channel opening, and (b) a medium-manifold system that includes a medium inlet for receiving a culture medium and a plurality of first connecting channels, each of the first connecting channels distributing the medium to the corresponding first chamber through the medium opening of the corresponding first chamber. Each of the first connecting channels is configured such that the culture medium exposed to the biological specimen received in the corresponding first chamber does not contact another biological specimen received in another first chamber. In addition, each of the first chambers is sized in a manner such that when the main channel system passes a seeding fluid containing a plurality of target biological specimens through the first channel segment, a first portion of the seeding fluid initially undergoes at a first flow rate through a first receiving chamber of the plurality of chambers and exits through the medium opening, and a second portion of the fluid undergoes at a second flow rate through the first receiving chamber after one of the target biological specimens becomes lodged with the first receiving chamber. The second flow rate is substantially less than the first flow rate so as to reduce the likelihood of a second target biological specimen entering the first receiving chamber.

In a yet another aspect, a microfluidic device comprises: (a) a main channel system having an inlet, an outlet, a central portion located between the inlet and the outlet, and a plurality of first chambers, the first chambers extending transversely to a first channel segment within the central portion, each of the first chambers having a channel opening that fluidly communicates with the first channel segment and a medium opening located away from the channel opening; and (b) a medium-manifold system having a medium inlet for receiving a culture medium and a plurality of first connecting channels, each of the first connecting channels distributing the culture medium to the corresponding first chamber through the medium opening of the corresponding first chamber. A seeding fluid comprising a plurality of target biological specimens flows from the inlet, through the first channel segment in a first direction to populate the first chambers with target biological specimens, to the outlet, and upon the first chambers being populated with target biological specimens, the culture medium flows past the target biological specimens in the first chambers toward the first channel segment and then within the first channel segment in a second direction that is opposite of the first direction.

In a yet another aspect, a microfluidic device comprises: (a) a main channel system having an inlet, an outlet, a central portion located between the inlet and the outlet, and a plurality of first chambers, the plurality of first chambers extending transversely to a first channel segment within the central portion, each of the plurality of first chambers having a channel opening that fluidly communicates with the first channel segment and a medium opening located away from the channel opening, each of the plurality of first chambers being located below the first channel segment in the direction of gravity during operation of the microfluidic device and being sized to contain at least one target biological specimen; and (b) a medium-manifold system having a medium inlet for receiving a culture medium and a plurality of connecting channels, each of the connecting channels distributing the medium to the corresponding chamber through the medium opening of the corresponding chamber, the culture medium flowing past the target biological specimen in each chamber so as to place a force thereon that is counteracted by the force of gravity on the target biological specimen.

In some embodiments of the microfluidic devices of various aspects described herein, the main channel system can further comprise a plurality of second chambers. The plurality of second chambers can extend transversely to a second channel segment within the central portion, where the second channel segment is connected to the first channel segment by an angled channel region. Each of the plurality of second chambers can have a channel opening that fluidly communicates with the second channel segment and a medium opening located away from the channel opening. In these embodiments, the medium-manifold system can further comprise a plurality of second connecting channels. Each of the second connecting channels can distribute a culture medium to the corresponding second chamber through the medium opening of the corresponding second chamber.

In some embodiments of the microfluidic devices of various aspects described herein, no connecting channels are configured to extend transversely from the central portion of the main channel system. Such configuration can prevent the fluid from one target biological specimen in a chamber contacting or contaminating other target biological specimens in other chambers. Meanwhile, fresh fluid can provide to each embryo without cross-talk or cross-contamination through the connecting channels. Since each embryo or a subset of embryos can be supplied and cultured with a different fluid (e.g., a culture medium comprising a different test agent) without cross-talk or cross-contamination, multiple (e.g., at least two or more) different test conditions can be performed in the same microfluidic device.

In some embodiments of the microfluidic devices of various aspects described herein, the central portion can comprise a plurality of channel segments along a pre-determined path. In one embodiment, the pre-determined path can comprise a serpentine path. Accordingly, in one aspect, a microfluidic device comprising a plurality of channel segments along a serpentine path is also provided herein. The microfluidic device comprises: (a) a main channel system having an inlet, an outlet, a central portion located between the inlet and the outlet, and a plurality of chambers, the central portion including a plurality of channel segments along a serpentine path, each of the plurality of channel segments having a set of the chambers extending transversely therefrom for receiving target biological specimens, each of the chambers in the set having a channel opening that fluidly communicates with the corresponding channel segment and a medium opening located away from the channel opening; and (b) a medium-manifold system having at least one medium inlet for receiving a culture medium and a plurality of connecting channels, each of the connecting channels distributing the culture medium to the corresponding chamber through the medium opening of the corresponding chamber. No connecting channels are configured to extend transversely from the central portion of the main channel system.

The microfluidic devices of various aspects described herein can be designed such that the target biological specimens received in the chambers can be all subjected to a single test condition or each subset of the target biological specimens can be subjected to a different test condition. For example, in some embodiments of various aspects described herein, the first and the second connecting channels in the microfluidic device can be configured to share the same medium inlet for receiving the same culture medium. In alternative embodiments, the first and the second connecting channels can be configured to have different medium inlets for receiving different culture media.

In some embodiments of various aspects described herein, the microfluidic device can further comprise a gradient generator fluidly connected upstream of the connecting channels. In some embodiments, the gradient generator can provide dilution of a test agent prior to delivery to the target biological specimens present in the chambers. In some embodiments, the gradient generator can be designed to provide a concentration gradient of a test agent prior to delivery to the target biological specimens present in the chambers. In these embodiments, each or subsets of the target biological specimens can be exposed to different concentrations of test agents, even when the first and the second connecting channels share the same medium inlet.

In some embodiments of various aspects described herein, the microfluidic device can further comprise at least one reservoir fluidly connected to the medium inlet(s). The reservoir can be external or integral to the microfluidic device.

Depending on types of the target biological specimen and/or measurements to be taken, different sensing devices can be incorporated into the chambers of the microfluidic devices described herein. For example, in some embodiments, the microfluidic device can further comprise at least one electrode in at least one or a plurality of the chambers.

In some embodiments of various aspects described herein, the microfluidic device can further comprise a main body and an optically transparent cover. The main body and the optically transparent cover define the main channel system and the medium-manifold system. For example, the optically transparent cover can comprise a gas-permeable sealing membrane.

The microfluidic devices described herein can be designed for culturing any biological specimen, for example, by sizing each of the chambers to receive a single target biological specimen. Examples of the target biological specimen can include, but are not limited to, a *Xenopus* or embryo thereof, a zebrafish or embryo thereof, a *C. elegans* or embryo thereof, a planaria or embryo thereof, a *Daphnia* or embryo thereof, a shrimp or embryo thereof, a *Drosophila* or embryo thereof, a tissue biopsy, an organoid, a cell, and a cell cluster. In some embodiments, the biological specimen can be genetically altered (e.g., with morpholios, siRNA, CRISPR and/or other gene-editing agents) or mutated to increase range of variation.

In some embodiments where the target biological specimen is *Xenopus* embryo, each of the chambers can be sized to receive a single *Xenopus* embryo that will develop in response to exposure to an agent introduced by flow of the culture medium. For example, in some embodiments, each of the chambers can have a depth that is less than the anticipated size of the *Xenopus* embryo after growth over a fixed time period such that at least a portion of the grown *Xenopus* embryo remains within the chamber after the fixed time period. In alternative embodiments, each of the chambers can have a depth that is longer than the anticipated size of the *Xenopus* embryo after growth over a fixed time period such that the grown *Xenopus* embryo remains entirely within the chamber after the fixed time period. In some embodiments, each of the chambers can have a width substantially equivalent to the anticipated size of the *Xenopus* embryo after growth over a fixed time period such that the grown *Xenopus* embryo has its ventral side or dorsal side up and remains unchanged in the orientation after the fixed time period. In one embodiment, the cross-section of the chambers can have a width of about 1.75 mm and a length of about 2.5 mm. In one embodiment, the chambers can also have a depth of about 8 mm.

A system for high through-put cell culture and/or assay/analysis is also provided herein. The system comprises: (a) a plurality of the microfluidic devices according to one or more embodiments described herein; (b) a plurality of holders, each of the plurality of holders configured to hold one or more of the plurality of the microfluidic devices such that the channel openings are located below the channel segments in the direction of gravity during operation of the microfluidic devices; and (c) a fluid handling module to control fluid flow in the main channel system and the medium-manifold system.

In some embodiments, the system can further comprise a detection module. An exemplary detection module includes, but is not limited to an imaging device. Non-limiting examples of the imaging device include brightfield, darkfield, phase-contrast, epifluorescence, fluorescence, microfluorimetry, confocal, multi-proton excitation microscopy, and a combination of two or more thereof. In some embodiments, the imaging device can be movably disposed along one or more axes, one of which is parallel to an axis along which the holders are disposed. The capability of the imaging device to move along one or more axes during imaging can enable automated analysis of a large number of target biological entities without further manipulation.

The holders can be designed to suit the need of different applications, e.g., "plug and play" function or imaging purpose. For example, in some embodiments, each of the plurality of holders can comprise a viewing window for viewing a target biological specimen in the chambers. In some embodiments, each of the plurality of holders can comprise a docking interface bearing one or more fluidic connectors configured to matingly and removably engage corresponding fluidic ports on the corresponding one of the plurality of the microfluidic devices. Thus, the microfluidic devices can be quickly set up for culture and/or analysis as soon as they are loaded into the holders. For example, a user does not have to connect fluidic tubing directly to the ports of the microfluidic devices every time when he/she sets up a new culture and/or assay in a new microfluidic device described herein.

In some embodiments, the plurality of holders can be independently disposed to translate along one or more axes. This can allow the microscope, even if the microscope is fixed at one location, to have optical assess to each chamber of the microfluidic device(s) when desirable. For example, the system can further comprise at least one rail along which at least one of the plurality of holders is disposed to translate.

The fluid handling module of the system is designed to control fluid flow rate and/or direction in the main channel system and the medium-manifold system of the microfluidic device(s) described herein during operation. In some embodiments, the fluid handling module can comprise a pump system. For example, the pump system can be configured to drive culture medium from a reservoir to supply nutrients to target biological specimen in the chambers through the connecting channels. The reservoir can be integrated or external to the microfluidic device. In some embodiments, the pump system can be configured to drive a fluid through the connecting channels at a flow rate sufficient to remove the embryo from the respective chambers. Pump systems for control of fluid delivery are known in the art and can be adapted in the system described herein. Examples of a pump system include, but are not limited to, a vacuum-driven system, a pressure-driven system, a peristaltic pump, a pneumatic pump, a mechanical pump, an acoustofluidic pump, an electrofluidic pump, and a combination of two or more thereof.

In some embodiments, the system can further comprise a robotic structure (e.g., a robotic arm) for interfacing with the microfluidic device for a specific purpose. For example, in one embodiment, the robotic structure can be configured for assessing or recovering the target biological specimen in the chambers. In this embodiment, the robotic structure can be configured to create an aperture in the optically transparent cover such that the target biological specimen received in the corresponding chamber is removed therefrom through the aperture. Alternatively or additionally, the robotic structure can be configured to collect a sample from the microfluidic device(s), and/or replenishing an on-device reservoir with fresh culture medium.

The inventors have discovered that, in one embodiment, vertical positioning of the microfluidic devices during operation provides optical and fluid handling access while stably maintaining the embryos in individual compartments in place (e.g., even with fluid flow) by gravity. Accordingly, in one embodiment, the holder can be configured to hold a microfluidic device in a direction that is parallel to the direction of gravity. However, the microfluidic devices can be also positioned at an angle of about 45 degrees relative to direction of gravity.

The microfluidic devices and/or systems described herein offer a number of advantages. For example, it can enable high-throughput separation of a large number of target biological specimens into individual compartments and/or chambers. As discussed above, the design of the microfluidic devices also allows for providing fresh culture medium to each target biological specimen in its respective chamber without cross-talk or cross-contamination. Thus, one can design an experiment to test a number of different test conditions in the same microfluidic device. Since the culture medium and target biological specimens are contained in a sealed device and/or system, it can also offer containment of toxic compounds, pathogens, and/or other hazardous materials introduced into the microfluidic device for testing. Further, the microfluidic devices and/or systems described herein allow for automated fluid handling and real-time analytical capability for a wide range of assays, including, e.g., but not limited to live/dead assays, bioelectrical state, and organ volumes/morphologies. In addition, the microfluidic devices and/or systems described herein allows for recovering the target biological specimens from their respective chambers for further analysis and/or culture. Accordingly, the microfluidic devices and/or systems described herein can be used for various cell-based culture and/or assay applications and methods of using the same are provided herein.

In one aspect, a high throughput method of trapping or separating single biological specimens is provided herein. Examples of the biological specimens include, but are not limited to *Xenopus* organisms or embryos thereof, zebrafish organisms or embryos thereof, *C. elegans* organisms or embryos thereof, planaria organisms or embryos thereof, *Daphnia* organisms or embryos thereof, shrimp or embryos thereof, *Drosophila* organisms or embryos thereof, a tissue biopsy, an organoid, a cell, a cell cluster, and genetic variants thereof. The method comprises: (a) providing at least one or more microfluidic devices described herein with the channel openings being located below the corresponding channel segment in the direction of gravity; (b) introducing a fluid comprising target biological specimens into the inlet of the main channel system; (c) causing the fluid to flow across the central portion in a first direction from the inlet to the outlet; and (d) allowing at least a portion of the biological specimens to individually enter into the chambers.

After the target biological specimens are separated into individual chambers, they can be cultured independently. For example, when the target biological specimens are embryos, e.g., of small organisms such as *Xenopus* or zebrafish, they can be cultured in the chambers to grow over a period of time. Accordingly, in some embodiments, the method can further comprise, after trapping the single biological specimens into the chambers, causing culture medium to enter the chambers through the connecting channels, thereby providing nutrients to the biological specimens via the corresponding medium openings.

In some embodiments, the method can further comprise causing a fluid to flow across the main channel via the central portion, e.g., to remove a sample (e.g., a fluid that has contacted the target biological specimens) or waste from the chambers. In particular, the fluid can be flown in a direction reverse to the first direction in which the fluid was flowing to separate the target biological specimens into individual chambers. This approach can enable the target biological specimens in their individual chambers to experience only culture medium introduced through the medium opening of the respective chambers, instead of fluid from the main channel that has contacted other target biological specimens. Thus, the reversal flow can minimize exposure of the trapped biological specimens to a fluid that have been in contact with other trapped biological specimens. Similar approach can be used to collect a fluid sample from the chambers having individual target biological specimens. The fluid sample can comprise conditioned culture medium, and/or secreted molecules and/or biological molecules (e.g., nucleic acid molecules, protein molecules) derived from the biological specimens.

In some embodiments, the target biological specimens in the chambers can be contacted with a test agent. Accordingly, another aspect provided herein relates to a method of determining an effect of one or a plurality of test agents on single biological specimens. Such method comprises: (a) providing at least one or more microfluidic devices described herein with the channel openings being located below the corresponding channel segment in the direction of gravity; (b) introducing a fluid comprising target biological specimens into the inlet of the main channel system; (c) causing the fluid to flow across the central portion; (d) allowing at least a portion of the biological specimens to individually enter into the chambers, thereby trapping single biological specimens in the chambers; (e) causing culture medium comprising at least one test agent to enter the chambers through the connecting channels, thereby exposing the biological specimens to the test agent via the medium openings of the corresponding chambers; and (f) detecting response of the biological specimens and/or assaying a sample from the chambers containing the biological specimens. Thus, an effect of the test agent(s) on the biological specimens can be determined.

As discussed above, since the culture medium and the target biological specimens are contained in a sealed device or system, any test agent, whether it is infectious, toxic, or pathogenic, can be tested using the microfluidic devices and/or systems described herein. Examples of a test agent include, but are not limited to proteins, peptides, nucleic acids, antigens, nanoparticles, environmental toxins or pollutants, carcinogens, small molecules, drugs or drug candidates, vaccine or vaccine candidates, pro-inflammatory agents, viruses, bacteria, unicellular organisms, cytokines, infectious agents, gene expression-modifying agents (e.g., morpholinos, siRNAs, CRISPR), and any combinations thereof.

Depending on the objective of an experiment, various analytical methods and/or assays can be performed to detect response of the biological specimens and/or to analyze a sample derived from the biological specimens of the chambers. Non-limiting examples of such analytical methods and/or assays include cell labeling, immunostaining, optical or microscopic imaging (e.g., immunofluorescence microscopy and/or scanning electron microscopy), gene expression analysis, cytokine/chemokine secretion analysis, metabolite analysis, polymerase chain reaction, immunoassays, ELISA, gene arrays, and any combinations thereof. For example, in one embodiment where the method described herein is designed to screen for teratogenic or anti-angiogenic activity of test agents such as chemicals or potential environmental toxins, imaging analysis of embryos that have been exposed to those test agents for detection of malformed embryos, inhibition in cell differentiation and/or inhibition in angiogenesis can be performed.

In some embodiments, at least a subset of the biological specimens present in their individual chambers can be exposed to an agent known to induce a disease-specific phenotype. Thus, each of those biological specimens develops into an individual disease model, e.g., for study of the disease, or for identification of a treatment. Thus, in some embodiments, the method can further comprise exposing the biological specimens, upon exposure to a disease-inducing agent, to a library of drug candidates in order to screen for a drug candidate that treats the disease-specific phenotype. Without limitations, the method described herein can be used to screened for tumor suppressors, regenerative repair inducers, compounds that counteract birth defects (e.g., induced by genetics and/or specific toxins), or compounds that modulate morphogenesis (e.g., for use in regenerative medicine), when the target biological specimens (e.g., embryos such as *Xenopus* embryos) are pre-exposed to an appropriate disease-inducing agent to induce a desirable disease-specific phenotype. For example, in one embodiment, the biological specimens pre-exposed to a known toxin or carcinogen can be exposed to a library of drug candidate to screen for an agent that reverses or reduces an effect of the known toxin or carcinogen on the biological specimens. Similarly, the biological specimens can be pre-exposed to an infectious agent, and then be contacted with a library of drug candidates to screen for tolerance, susceptibility or resistance to the infectious agent.

As discussed above, one of the advantages of the microfluidic devices and/or systems described herein is that target biological specimens can be separated into individual chambers. Thus, the diversity of a population of target biological specimens can be maintained by preventing rare biological specimens being outcompeted by dominant target biological specimens. As such, rare biological specimens can be identified and methods of achieving such purpose are also described herein. The method of identifying a rare biological specimen from a sample comprising: (a) providing at least one or more microfluidic devices described herein with the channel openings being located below the corresponding channel segment in the direction of gravity; (b) introducing a sample comprising biological specimens to be assayed into the inlet of the main channel system; (c) causing the fluid to flow across the central portion; (d) allowing the biological specimens to individually enter into the chambers, thereby separating single biological specimens into the chambers; and (e) assaying the biological specimens in the chambers and/or assaying an aliquot of culture medium from the chambers containing the biological specimens, thereby identifying a rare biological specimen from the sample.

To identify a rare biological specimen, different cell and/or molecular assays can be performed to analyze behavior of the biological specimens and/or molecules secreted by the biological specimens, including, e.g., but not limited to cell labeling, immunostaining, optical or microscopic imaging (e.g., immunofluorescence microscopy and/or scanning electron microscopy), gene expression analysis, cytokine/chemokine secretion analysis, metabolite analysis, polymerase chain reaction, immunoassays, ELISA, gene arrays, or any combinations thereof.

In some embodiments, the method can further comprise performing whole genome sequencing of the identified rare biological specimen.

In some embodiments, the method can further comprise growing the identified rare biological specimen to a larger population.

The microfluidic devices and/or systems described herein can be also be used to grow stem cell organoids and identify appropriate stem cell organoids for various clinical applications. In one aspect, a method of growing a stem cell organoid comprises: (a) providing at least one or more microfluidic devices described herein with the channel openings being located below the corresponding channel segment in the direction of gravity; (b) introducing a sample comprising stem cells into the inlet of the main channel system; (c) causing the fluid to flow across the central portion; (d) allowing at least one or more stem cells to enter into the chambers, thereby trapping at least one or more stem cells in the chambers; and (e) culturing the stem cells in the respective chambers for a period of time such that the stem cells differentiate and form an organoid. To identify a stem cell organoid for a target application, the method can further comprise assaying the organoid in the respective chambers and/or assaying an aliquot of culture medium from the chambers containing the organoid using any art-recognized cell and/or molecular assays.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 2A shows an overview of the system housed in an environment-controlled enclosure (e.g., a temperature and carbon dioxide-controlled enclosure). FIG. 2B shows various perspective views of some components of the system.

FIG. 3A shows filling the main channel system with a fluid. FIG. 3B shows introducing embryos through the inlet into the central portion and individual embryos entering into respective chambers. FIG. 3C shows reversed flow in the main channel system while the medium-manifold system supplying culture medium to the chambers through the medium opening of the corresponding chambers.

Figure 1:
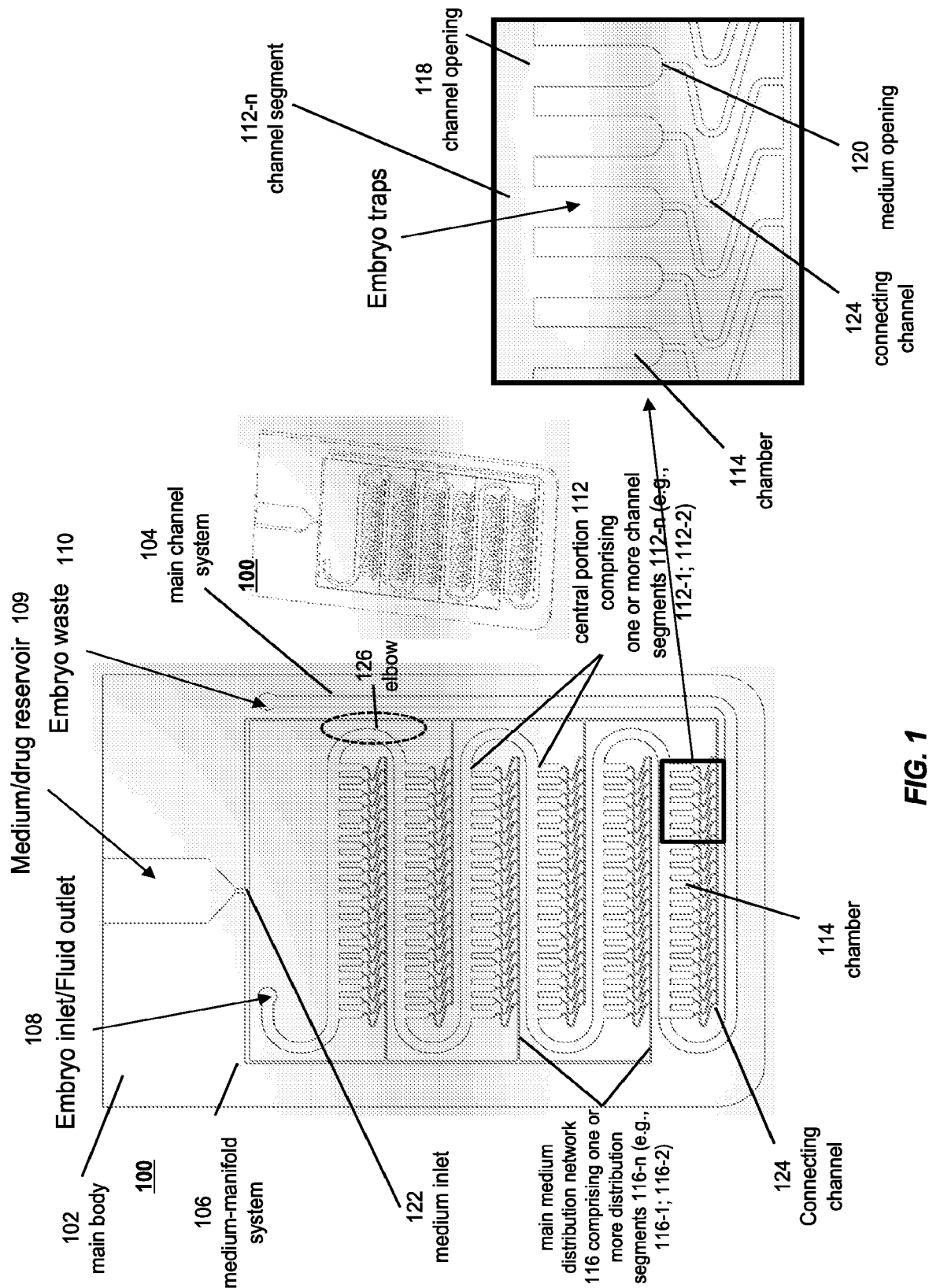
FIG. 1 is a schematic diagram showing a front view or top view of a microfluidic device according to one embodiment described herein for high-throughput cell culture. In one embodiment, the microfluidic device can be used for high-throughput *Xenopus* culture. The inset is a schematic diagram showing a magnified view of a plurality of the chambers for trapping or receiving single target biological specimens, e.g., embryos, and the associated connecting channels.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

It should be understood that the inventions described herein are not limited to the particular methodology, protocols, and reagents, etc., described herein and as such may vary. The terminology used herein is for the purpose of describing particular embodiments only, and is not intended to limit the scope of various embodiments described herein, which is defined solely by the claims.

As used herein and in the claims, the singular forms "a", "an" and "the" include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Aspects of the present disclosure relate to microfluidic devices and/or systems that allow rapid trapping of single target biological specimens in a high-throughput manner and/or screening of a large number of individual target biological specimens for various cell-based assay applications, including, e.g., but not limited to high-density cell culture, identifying molecular targets, drug screening, and/or identifying rare biological specimens. By way of example only, the devices and/or systems can be used to identify specific specimens of desirable phenotypes (e.g., to identify susceptible, resistant, or tolerant specimens (e.g., embryos)) for further manipulation and/or analysis. Alternatively or additionally, the devices and/or systems can be used to screen a library of drugs (e.g., ion channel drugs) on target biological specimens to identify drugs that confer optimal tolerance.

As an example, the inventors have developed a microfluidic device that can rapidly separate at least about 100-250 embryos into ordered, indexed arrays with embryos geometrically constrained for optimal imaging, and can also allow optical access for automated imaging using various imaging modalities, e.g., brightfield and/or fluorescence modalities. In addition, the microfluidic device is designed such that each target biological specimen (e.g., embryo) receives fresh fluid that has not been contacted by other biological specimens (e.g., embryos). For example, fresh medium can be directly delivered to the embryos without prior embryo exposure, which meets Institutional Animal Care and Use Committee (IACUC) guidelines for *Xenopus* care. This feature is beneficial to various applications, e.g., in a robust analysis of pathogen response where large numbers of embryos can be susceptible to dying and cross-talk between embryos, e.g., due to an embryo death, could significantly affect the outcome of an assay. Moreover, a fluid pump system (e.g., but not limited to a vacuum driven system) can deliver a fluid (e.g., culture medium) from an on-device reservoir across the target biological specimens (e.g., embryos). In addition, by loading (e.g., in a "plug and play" manner) a plurality of (e.g., at least 2 or more, including, e.g., at least 2, at least 3, at least 4, at least 5, at least 6, at least 7, at least 8, at least 9, at least 10, or more) microfluidic devices as described herein into an automated fluid handling and imaging instrument, a high-throughput system can be developed to enable rapid trapping of at least about 1,200 to about 2000 embryos (e.g., *Xenopus* embryos) per experiment followed by in situ parallel culture (e.g., for a duration of about 3-7 days) and screening of the embryos on-device (e.g., repeated imaging over a period of time) or off-device. In some embodiments, the system can provide full cell and/or embryo culture capabilities, including, e.g., but not limited to medium exchange/perfusion, pH, oxygen, temperature, and/or medium quality logging and maintenance. Accordingly, embodiments of various aspects described herein relate to microfluidic devices and systems for high-throughput cell culture and/or assays as well as uses thereof.

Exemplary Microfluidic Devices for High-Throughput Cell Culture and/or Assay

Some aspects described herein relate to microfluidic devices for high-throughput cell culture and/or assay. Generally, the microfluidic devices described herein comprises (a) a main channel system having an inlet, an outlet, a central portion located between the inlet and the outlet, and a plurality of chambers, the chambers extending transversely to a channel segment within the central portion, each of the chambers having a channel opening that fluidly communicates with the channel segment and a medium opening located away from the channel opening; and (b) a medium-manifold system having a medium inlet for receiving a culture medium and a plurality of connecting channels, each of the connecting channels distributing the culture medium to the corresponding chamber through the medium opening of the corresponding chamber.

To minimize or avoid the culture medium exposed to the biological specimen received in a chamber contacting another biological specimen received in another chamber, the connecting channels are configured such that they do not receive any fluid from the channel segment of the central portion. For example, no connecting channel is configured to extend transversely from a central portion of the main channel system. That is, each connecting channel does not act as a direct interconnecting structure between the medium opening of the corresponding chamber and a downstream channel segment of the central portion, e.g., a channel segment that is located below the same medium opening in the direction of gravity during operation of the microfluidic device. Such configuration can prevent the fluid from one target biological specimen in a chamber contacting or contaminating other target biological specimens in other chambers. Meanwhile, fresh fluid can be provided to each embryo without cross-talk or cross-contamination through the connecting channels. Since each embryo or a subset of embryos can be supplied and cultured with a different fluid (e.g., a culture medium comprising a different test agent) without cross-talk or cross-contamination, multiple (e.g., at least two or more) different test conditions can be performed in the same microfluidic device.

For the illustrative purposes only and by no means to be construed as limiting in the scope of embodiments of various aspects described herein, references will be made to some embodiments illustrated in the drawing. The inventions described herein include any alterations and further modifications in the illustrated microfluidic devices and further applications of the principles of the inventions which would normally occur to one skilled in the art to which the inventions relate.

Referring now to FIG. 1, one embodiment of a microfluidic device is illustrated. The microfluidic device 100 includes a main body 102, and a main channel system 104 and a medium-manifold system 106 disposed therein. The main channel system 104 is configured to provide a fluidic passageway for separating a plurality of target biological specimens into individual compartments. The medium-manifold system 106 is configured to provide a fluidic passageway for supplying a fluid (e.g., a culture medium optionally comprising a test agent) to individual target biological specimens.

The main body 102 can be made of any polymeric or glass materials, or any materials that are compatible with cell culture reagents and target biological specimens to be cultured therein. In some embodiments, optically transparent materials can be desirable, e.g., for optical imaging. Exemplary polymeric materials that can be used in the main body include, but are not limited to, polyurethanes, rubber, molded plastic, polymethylmethacrylate (PMMA), polycarbonate, polytetrafluoroethylene (TEFLON™), polyvinylchloride (PVC), polydimethylsiloxane (PDMS), polysulfone, and a combination of two or more thereof. The ether-based, aliphatic polyurethane described in the International Application Publication No. WO/2012/154729, the content of which is incorporated herein by reference, can also be used to fabricate the main body.

In some embodiments, the material for the main body 102 can be selected and/or modified to suit a particular application. By way of example only, for optical imaging analysis, the material for the main body can be transparent at one or more desired wavelengths. For culture and release of target biological specimens (e.g., organisms, organoids, etc.), any biocompatible material can be used. In some embodiments, low surface binding can be desirable if protein analysis is to be performed; this can be accomplished by material selection and/or by surface treatment, such as coating or oxidation. In some embodiments, gas permeability can be accomplished by having a gas permeable seal onto the main body. This permits the body to have any gas permeability. To use the microfluidic devices described herein for studies of oxygen requirements or effects, the main body material should be largely impermeable to gas. For application of culture and/or analysis of *Xenopus* embryos, the main body material can be selected for clarity, biocompatibility, and/or compatibility with rapid manufacturing methods. Examples of such materials that can be used for *Xenopus* embryo applications include, but are not limited to PDMS, polycarbonate, cycloolefin, polystyrene, and a combination of two or more thereof. In some embodiments, the microfluidic devices can be plasma treated for sterility, hydrophilicity, or a combination thereof, such as an initial plasma treatment prior to loading of the fluids and the biological specimens.

The main channel system 104 has an inlet 108, an outlet 110, a central portion 112 located between the inlet 108 and the outlet 110, and a plurality of chambers 114 extending transversely to a channel segment (e.g., a first channel segment 112-1) within the central portion 112. The central portion 112 is a channel, a conduit, or a duct defining a passageway through and along which a fluid flows, passes or moves between the inlet 108 and the outlet 110. The channel comprises at least one or a plurality (e.g., at least two or more) channel segments 112-$n$ (e.g., 112-1 representing a first channel segment; and 112-2 representing a second channel segment). Accordingly, in some embodiments, the main channel system 104 can comprise a first channel segment 112-1 with a plurality of first chambers 114 extending transversely therefrom, and a second channel segment 112-2 with a plurality of second chambers 114 extending transversely therefrom. The first channel segment 112-1 and the second channel segment 112-2 can be fluidly connected by any means, e.g., by a channel segment connector, e.g., an elbow connector as described below.

It should be noted that during operation, the central portion 112 is not only used to flow a fluid comprising target biological specimens for separation of the target biological specimens into individual chambers, but is also used to allow a fluid, e.g., a culture medium, flowing across in order to carry away secretion and/or waste from the target biological specimens, which can be either discarded or collected as a sample for analysis. The latter fluid flow is reversed in direction from that of the former fluid flow to separate target biological specimens into individual chambers. The capability of reversing a fluid flow can allow for a single inlet for introducing target biological specimens and removing any excess target biological specimens, as well as enabling the target biological specimens disposed in the chambers to experience only fresh culture medium (with or without test agents and/or molecules) received by the medium inlet, not "exposed" fluid that has contacted other target biological specimens in other chambers. Accordingly, the inlet 108 as shown in FIG. 1 acts as an inlet for introducing target biological specimens and also as a medium outlet for an "exposed" fluid, while the outlet 110 is an outlet for removal of excess target biological specimens.

The channel segments can be arranged in any configuration to provide a channel of any tortuosity or of any path pattern. Thus, the passageway defined by the channel and/or channel segments of the central portion 112 can be of any tortuosity or of any path pattern. For example, in some embodiments, the passageway can be designed to form a curved pathway, e.g., to maintain the compactness of the microfluidic device while allowing for a high density of chambers for cell culture in the microfluidic device. By way of example only, FIG. 1 shows one embodiment of the microfluidic device described herein with the central portion 112 defining a serpentine-like passageway such that each channel segment along the serpentine-like path can allow a plurality of chambers to extend transversely therefrom for receiving target biological specimens. Stated another way, in some embodiments, the central portion 112 and/or channel segments 112-$n$ can comprise a combination of linear pathways and curved pathways. For example, the serpentine-like pathway shown in FIG. 1 can be construed as a combination of linear pathways and curved pathways where every two linear pathways are connected by a curved pathway. While the curved pathway connecting the two linear pathways as shown in FIG. 1 comprises a smooth (no pointed angle) elbow, the elbow can also form a sharp angle. The term "elbow" as used herein refers to a structural feature with at least one side of a surface having a bend such that it directs a fluid flow through a smooth or sharp angle between 0 degrees and 180 degrees, including, for example, between 45 degrees and about 135 degrees. In some embodiments, the elbow can direct a fluid flow through a smooth or sharp angle of about 90 degrees. In some embodiments, the elbow can direct a fluid flow through a combined angle of about 180 degrees, i.e., the direction of the fluid flow after the elbow is substantially opposite to the direction of fluid flow before the elbow. In these embodiments, the elbow can have a U-shaped structure, e.g., as shown in FIG. 1. The elbow 126 can be located anywhere along the passageway defined by the central portion 112 of the main channel system 104.

However, other patterns such as linear paths with or without branching can also be used to design the configuration of the central portion 112. For example, in some embodiments, the central portion 112 can be configured to provide one or a plurality of (e.g., at least two or more) linear paths. When there are more than one linear paths within the central portion 112, the linear paths can share the same inlet 108 and/or the same outlet 110, and/or at least some or all having different inlets 108 and/or outlets 110. In some embodiments, the central portion 112 can be configured with initial path branching followed by respective paths (e.g., linear paths or paths of any pattern).

The main channel system 104 can be disposed in the microfluidic device described herein as an isolated or self-contained fluidic system by itself (e.g., as shown in FIG. 1), or as part of a 2-D array of other independent fluidic system(s) (but not part of the medium-manifold system described herein) disposed in the same microfluidic device or fluidly connected to a separate microfluidic device.

The number of chambers 114 extending from a path of the central portion of the main channel system can vary depending on the dimension of the main body 102, the path length of the central portion 112, the chamber size, and/or the desired throughput of the device. For example, when the main body has a dimension of a typical microscopic slide (e.g., about 3 inches by about 1 inch), the main channel system can be configured to have at least about 10 chambers or more, including, e.g., at least about 15 chambers, at least about 20 chambers, at least about 30 chambers, at least about 40 chambers, at least about 50 chambers, or more. Accordingly, in some embodiments, the number of chambers extending from a path of the central portion can be more than 50 chambers or fewer than 10 chambers, e.g., based on the need of an application and/or the dimensions of the main body.

The length of the central portion 112 and/or channel segments 112-$n$ can be of any dimension. The longer the central portion 112 and/or channel segment 112-$n$ is, the more the number the chambers can be placed along the central portion and/or channel segment, thus providing a high-density cell culture microfluidic device. In some embodiments, the central portion 112 can have a length of about 60 mm.

The cross-section of central portion 112 and/or channel segments 112-$n$ can be of any dimension, which can vary, e.g., with flow rate and/or volume of a fluid to be flown through and aspects ratio and/or the length of the central portion and/or channel segments. In some embodiments, the cross-section of the central portion 112 and/or channel segments 112-$n$ can have a dimension ranging from about 20 μm to about 3 mm, from about 30 μm to about 2 mm, from about 50 μm to about 1000 μm, from about 100 μm to about 750 μm, or from about 200 μm to about 500 μm. The cross-section of the central portion 112 and/or channel segments 112-$n$ can be of any shape, e.g., a circle, an ellipse, a triangle, a square, a rectangle, a polygon or any irregular shape. In some embodiments, the central portion 112 and/or channel segments 112-$n$ can have a circular cross-section. In other embodiments, the central portion 112 and/or channel segments 112-$n$ can have a square cross-section.

The cross-sectional dimensions of the central portion 112 and/or channel segments 112-$n$ can vary with the size of target biological specimens to be captured. In general, the channel cross-sectional dimensions can be driven by the dimensions of target biological specimens to be capture with added space to avoid clogging or specimen damage. By way of example only, for single cells or small organoids, the cross-sectional dimensions of the central portion 112 and/or channel segments 112-$n$ can go as low as 20-30 μm. For more mature embryos, e.g., of fish or xenopus, the cross-section of the central portion 112 and/or channel segments 112-$n$ can have a dimension closer to 2-3 mm. For example, in one embodiment involving *Xenopus* embryo application, the cross-section of the central portion 112 and/or channel segments 112-$n$ should accommodate a *Xenopus* embryo, which is roughly 1-1.5 mm in diameters. Accordingly, in some embodiments, the square cross-section of the central portion 112 and/or channel segments 112-$n$ for *Xenopus* embryo application can have a dimension of about 1.75 mm.

The chambers can be spaced apart from each other along a path of the central portion of the main channel system by any appropriate distance provided that no more than one target biological specimen enters into a chamber. The spacing between any two chambers can be constant or vary along the path of the central portion. Generally, the spacing between any two chambers should not affect performance of the microfluidic device to trap a single biological entity therein and/or subsequent cell culture.

The chambers 114 extend transversely to a channel segment 112-$n$ within the central portion 112. In embodiments of the microfluidic device herein, the plurality of the chambers 114 can extend at any angle transverse to the channel segment 112-$n$ within the central portion 112. In some embodiments, the plurality of the chambers 114 can extend from either side of the channel segment 112-$n$ at an angle between 0 and 180 degrees, between 45 and 135 degrees or between 60 and 120 degrees. In some embodiments, the plurality of the chambers 114 can extend perpendicularly from either side of the channel segment 112-$n$. In some embodiments, the chambers 114 extend transversely to a linear channel segment 112-$n$ within the central portion 112.

In some embodiments, each chamber 114 can be located below a corresponding channel segment 112-$n$ in the direction of gravity during operation of the microfluidic device described herein.

Each of the chambers 114 having a channel opening 118 that fluidly communicates with the channel segment 112-$n$ and a medium opening 120 located away from the channel opening 118. As used herein, the term "fluidly communicates" or "fluidly connects" between two components (e.g., the channel opening 118 and the channel segment 112-$n$) or equivalent thereof means that a fluid (e.g., gas or liquid) can flow from one component (e.g., channel opening 118) to another (e.g., the channel segment 112-$n$) but does not exclude an intermediate component between the two recited components which are in fluid communication. In some embodiments, the two components (e.g., the channel opening 118 and the channel segment 112-$n$) are integral to each other. In some embodiments, the two components (e.g., the channel opening 118 and the channel segment 112-$n$) can be fluidly connected by an intermediate component, e.g., a fluidic channel.

The channel opening 118 can be sized according to the dimensions of a target biological specimen to be received by the chamber. In some embodiments, the channel opening 118 and the chamber 114 can have the same cross-sectional dimensions, e.g., as shown in FIG. 1. However, in some embodiments, the channel opening 118 can have smaller cross-sectional dimensions than those of the chamber 114. For example, as the target biological specimens are generally smaller in size when they are being separated into individual chambers than when they later grow in the chambers upon separation, the chambers can be sized to accommodate the desired size to which the target biological specimen grows, while the channel opening can be sized smaller as long as the channel opening size is sufficient to permit the target biological specimen to enter the chamber. In some embodiments, the channel opening 118 can have larger cross-sectional dimensions than those of the chambers 114.

While the chambers 114 can have any size, the depth of the chambers should be configured such that the distance between the target biological specimen (e.g., embryos, tissues, and/or cells) received in the chambers and the channel segment 112-$n$ above the chamber 114 is sufficiently long enough to avoid the target biological specimen from contacting or exposing to an agent or molecule present in the channel segment 112-$n$, e.g., due to diffusion. As described earlier, the central portion 112-$n$ is not only used to flow a fluid comprising target biological specimens for separation of the target biological specimens into individual chambers, but is also used to allow a fluid, e.g., a culture medium, flowing across in order to carry away secretion and/or waste from the target biological specimens, which can be either discarded or collected as a sample for analysis. Accordingly, it is desirable to design the depth of the chambers such that the individual target biological specimens can be isolated from each other without contact from or exposure to secretion and/or waste of other target biological specimens, e.g., due to diffusion. For example, the distance between the target biological specimen (e.g., embryos, tissues, and/or cells) received in the chambers and the channel segment 112-$n$ above the chamber 114 can be a function of input fluid flow rate into each chamber and diffusion time of agents and/or molecules. In some embodiments, the distance between the target biological specimen (e.g., embryos, tissues, and/or cells) received in the chambers and the channel segment 112-$n$ above the chamber 114 can be at least about 5 mm or longer, including, e.g., at least about 6 mm, at least about 7 mm, at least about 8 mm, at least about 9 mm, at least about 10 mm, at least about 15 mm or longer. In some embodiments, the distance between the target biological specimen (e.g., embryos, tissues, and/or cells) received in the chambers and the channel segment 112-$n$ above the chamber 114 can be about 5 mm to about 10 mm. However, such distance can vary depending on the diffusion time of agents/molecules in the fluid and/or actual flow rates/flow transit times across the chambers 114. In some embodiments, the depth of the chambers can be of any dimension provided that there is no significant imaging difficulty (e.g., induced by plane of focus and/or meniscus distortion effects).

In some embodiments, without wishing to be bound by theory, deep chambers can affect specimen trapping, as the impact of a single specimen may not be enough to adequately block the flow of fluid into the connecting channels 124. An exemplary design guideline is to size the depth of the chamber relative to a target biological specimen to be captured. For example, a 1 mm specimen can have a 1.25-2 mm deep chamber 114. A rough estimate of the chamber depth can be about 1 times to about 5 times, or about 1.25 times to 2 times, of the length of a target biological specimen. In some embodiments, a rough estimate of the chamber length can be at least 1× and probably not more than 5× of the largest specimen dimension.

In some embodiments, the depth of the chambers 114 can be decreased to permit captured target biological specimens exposed into the central portion 112 or channel segments 112-$n$. In some embodiments, since the microfluidic devices described herein can be run "in reverse" in that the direction of flow is never changed from the trapping direction, this can be used to look for organismal variation in response to soluble compounds and/or to sample each organism's byproducts using the connecting channels if they were redesigned to not be connected to each other. In some embodiments, the microfluidic devices with the chamber length shorter than the length of target biological specimens (provided that the capture target biological specimens do not fall out of the chambers, which can be accomplished by maintaining the microfluidic devices described herein vertically during operation) can be used for chemoattractant studies and/or for population sensing akin to quorum sensing in bacteria or pheromone interactions.

The entire depth of each chamber is the sum of the desired size of a target biological specimen and the distance between the target biological specimen (e.g., embryos, tissues, and/or cells) received in the chambers and the channel segment 112-n above the chamber. In some embodiments, each chamber can have a depth that is at least 50% or more (including, e.g., at least about 60%, at least about 70%, at least about 80%, at least about 90%, at least about 95%, at least about 1.1-fold, at least about 1.5-fold, at least about 2-fold, at least about 3-fold or more) longer than the anticipated size of the target biological specimen after growth over a fixed time period such that the grown target biological specimen remains entirely within the chamber after the fixed time period. In one embodiment, the entire depth of the chambers can be about 8 mm.

In some embodiments, the depth of the chambers can be configured to generate a diffusion gradient of a test agent or molecule along the length of the target biological specimens disposed in the respective chambers. For example, in these embodiments, a diluent (e.g., a buffered solution or a plain culture medium) can be introduced from the outlet 110 and flows through the central portion 112 from the outlet 110 to the inlet 108, while a fluid comprising a test agent or molecule can be introduced to the target biological specimens within the respective chambers through the medium openings 120 via the respective connecting channels 124. The presence of a diluent flow in the central portion 112 can result in a concentration gradient of the test agent due to diffusion of the test agent into the central portion 112.

In some embodiments, the cross-section of each chamber 114 can be sized to receive a single target biological specimen from the channel segment 112-n. Accordingly, one aspect provided herein relates to a microfluidic device described herein with a plurality of chambers being sized to receive a single target biological specimen from the channel segment. For target biological specimens (e.g., embryos and/or cells) that will grow in size over time or develop in response to exposure to an agent introduced by flow of a culture medium, the chambers 114 can be sized to the desired size of a target biological specimen that it may reach over a pre-determined period of time. The pre-determined period of time can vary based on a number of factors, including, e.g., the maturation or growth period of the target biological specimen and/or the experiment duration. In some embodiments, the pre-determined period of time can be at least 3 days, at least 4 days, at least 5 days, at least 6 days, at least 1 week, at least 2 weeks, at least 3 weeks, at least 4 weeks, at least 2 months, at least 3 months or longer.

In some embodiments of this aspect and other aspects described herein, the cross-section of each chamber 114 can be sized to geometrically constrain the target biological specimen as it grows such that the growing target biological specimen can be oriented only in a limited number of positions, e.g., limiting the target biological specimen to have one particular side facing the channel opening. For example, fertilized oocytes can be loaded as spheres and separated into individual chambers, in which each oocyte is subsequently developed into an oblong embryo, after a period of about 7 days, having either its ventral side or dorsal side facing the channel opening, due to the geometric constraint of the chambers. In this design, the oblong embryos are unlikely able to re-orient into another position within the chambers. Such design constraint can allow for easier imaging without further manipulations and thus enable automated imaging, as compared to designs where the target biological specimen can grow in the chamber and end up in various orientations due to no confinement during their growth.

In some embodiments, the cross-sectional dimension of the individual chambers can be comparable to the diameter of a well in a 24-well plate. In some embodiments, the cross-sectional dimension of the individual chambers can be comparable to the diameter of a well in a 48-well plate.

To ensure that each chamber receive a single target biological specimen, each of the chambers can be sized in a manner such that when the main channel system passes a seeding fluid containing a plurality of target biological specimens through a channel segment, a first portion of the seeding fluid initially undergoes at a first flow rate through a first receiving chamber of the chambers and exits through the medium opening. When a second portion of the fluid undergoes at a second flow rate through the first receiving chamber after one of the target biological specimens becomes lodged with the first receiving chamber, the second flow rate is substantially less than the first flow rate so as to reduce the likelihood of a second target biological specimen entering the first receiving chamber. Accordingly, one aspect of the microfluidic devices described herein relates to a microfluidic device with a plurality of chambers being sized in the aforementioned manner.

In some embodiments of this aspect and other aspects described herein, the cross-section of the chambers can range from about 1 mm to about 5 mm, or from about 1.5 mm to about 3 mm. In one embodiment, the chambers can have a cross-section of about 1.75 mm (width)× about 2.5 mm (length). The cross-section of the chambers can be of any shape, including, e.g., but not limited to circular, rectangular, square, polygon, or irregular shaped.

The microfluidic devices described herein can be designed for culturing any biological specimen, for example, by sizing each of the chambers to receive a single target biological specimen. Examples of the target biological specimen can include, but are not limited to, a *Xenopus* or embryo thereof, a zebrafish or embryo thereof, a *C. elegans* or embryo thereof, a planaria or embryo thereof, a *Daphnia* or embryo thereof, a shrimp or embryo thereof, a *Drosophila* or embryo thereof, a tissue biopsy, an organoid, a cell, and a cell cluster. In some embodiments, the biological specimen can be genetically altered (e.g., with morpholios, siRNA, CRISPR and/or other gene-editing agents) or mutated to increase range of variation.

In some embodiments of this aspect and other aspects described herein, where the target biological specimen comprises embryos, e.g., *Xenopus* embryos, each of the chambers 114 can be sized to receive a single *Xenopus* embryo that will grow or develop in response to exposure to an agent introduced by flow of the culture medium over a period of time. For example, in some embodiments, each of the chambers can have a width substantially equivalent to the anticipated size of the Xenpus embryo after growth over a fixed time period (e.g., at least about 7 days or longer) such that the grown *Xenopus* embryo has its ventral side or dorsal side up and remains unchanged in the orientation after the fixed time period. In one embodiment, the chambers can have a cross-section of about 1.75 mm (width)× about 2.5 mm (length). In some embodiments, each of the chambers can have a depth that is less than the anticipated size of the *Xenopus* embryo after growth over a fixed time period such that at least a portion of the grown *Xenopus* embryo remains within the chamber after the fixed time period. In some embodiments, each of the chambers can have a depth that is longer than (e.g., at least about 50% or more longer than, including, e.g., at least about 60%, at least about 70%, at least about 80%, at least about 90%, at least about 95%, at least about 1.1-fold, at least about 1.5-fold, at least about 2-fold, at least about 3-fold or more, longer than) the anticipated size of the *Xenopus* embryo after growth over a fixed time period (e.g., at least about 1 week or longer) such that the grown *Xenopus* embryo remains entirely within the chamber after the fixed time period.

Each chamber 114 has a medium opening 120. While FIG. 1 shows that the medium opening 120 is located directly opposite to the channel opening 118, it is not construed to be limiting. For example, in some embodiments, the medium opening 120 can be located along the side of the chamber 114 provided that the medium opening 120 is located sufficiently far away from the channel opening 118 such that a fluid introduced through the medium opening 120 can contact the target biological specimen in the chamber 114 before it gets carried away by a fluid flowing across the channel opening 118. The ability to have the inflow be aimed at different regions or portions of the target biological specimen (e.g., an embryo) can be desirable, for example, if imaging provides information on which way the target biological specimen (e.g., an embryo) is facing relative to the chamber opening or medium opening.

In some embodiments of this aspect and other aspects described herein, there can be more than one medium openings 120, e.g., two medium openings or more, that fluidly communicate with the corresponding chamber 114. For example, one medium opening 120 can be used to introduce a basic culture medium into the chamber 114. Another medium opening 120 can be used to introduce a test agent. In some embodiments, one end portion of the connecting channel 124 leading to the corresponding chamber 114 can be split to form two or more medium openings 120 in the chamber 114. This can provide a more uniform distribution of an agent or culture medium or a local stable concentration gradient.

In some embodiments, dimensions of the medium opening(s) 120 can range from 10 μm or less up to the smallest dimension of a target biological specimen, with a desirable range roughly 10% or less of the smallest specimen dimension. In some embodiments, the dimensions of the medium opening(s) can be 200 μm by 300 μm.

Referring to FIG. 1, the medium-manifold system 106 of the microfluidic devices described herein includes at least one or more medium inlet 122 and a plurality of connecting channels 124. The medium inlet 122 is designed to receive a fluid to be introduced into the target biological specimen disposed in each chamber. In some embodiments, the fluid received by the medium inlet 122 can be a culture medium to maintain or promote the growth and/or culture of the target biological specimen. In some embodiments, the fluid received by the medium inlet 122 can further comprise a test agent or molecule such that effects of the test agent or molecule on the target biological specimen can be measured or detected. The test agent or molecule can be mixed into the cell culture medium or introduced separately. Accordingly, in some embodiments, the medium-manifold system 106 can comprise at least two or more (including, e.g., at least three or more, at least four or more) medium inlets 122. In these embodiments, one of the medium inlets can be adapted for receiving a culture medium (e.g., a control medium without any test agent or molecule), while the other medium inlet(s) can be adapted for receiving a fluid comprising a test agent or molecule). Alternatively, one of the medium inlets can be adapted for receiving a first fluid or cell culture medium comprising a first test agent or molecule, while the other medium inlet(s) can be adapted for receiving a second fluid or cell culture medium comprising a second test agent or molecule. In such embodiments, the target biological specimens disposed in the individual chambers can be arranged into populations exposing to different test agents or molecules in a single microfluidic device.

The medium inlets 122 can be fluidly connected to a reservoir for culture medium (with or without a test agent or molecule) that is integrated into the same microfluidic device or is separated from the microfluidic device. For illustration purpose only, FIG. 1 shows a medium inlet 122 fluidly connected to an on-device reservoir 109 integrated into the microfluidic device 100. In other embodiments, the medium-manifold system 106 can comprise a medium inlet port that fluidly connects a medium inlet 122 to a reservoir that is separated from the microfluidic device. As used herein, the term "port" refers to an opening into or through a structural component for the passage of a fluid.

In some embodiments of this aspect and other aspects described herein, the microfluidic device described herein can further comprise a reservoir fluidly connected to the medium inlet(s). As used herein, the term "reservoir" refers to a chamber for holding a culture medium (with or without a test agent or molecule). The reservoir chamber can be of any size, e.g., large enough to supply a culture medium (with or without a test agent or molecule) over a fixed period of time. For example, in one embodiment, a reservoir of about 1-3 mL can allow for a culture time that is suitable for multi-day standalone culture. With automated fluid handling, smaller (e.g., 0.5 mL) reservoirs can be used. It should be noted that the reservoir volume is, in part, designed based on the consumption rate and desired time between refills.

Figures 3A, 3B, 3C:
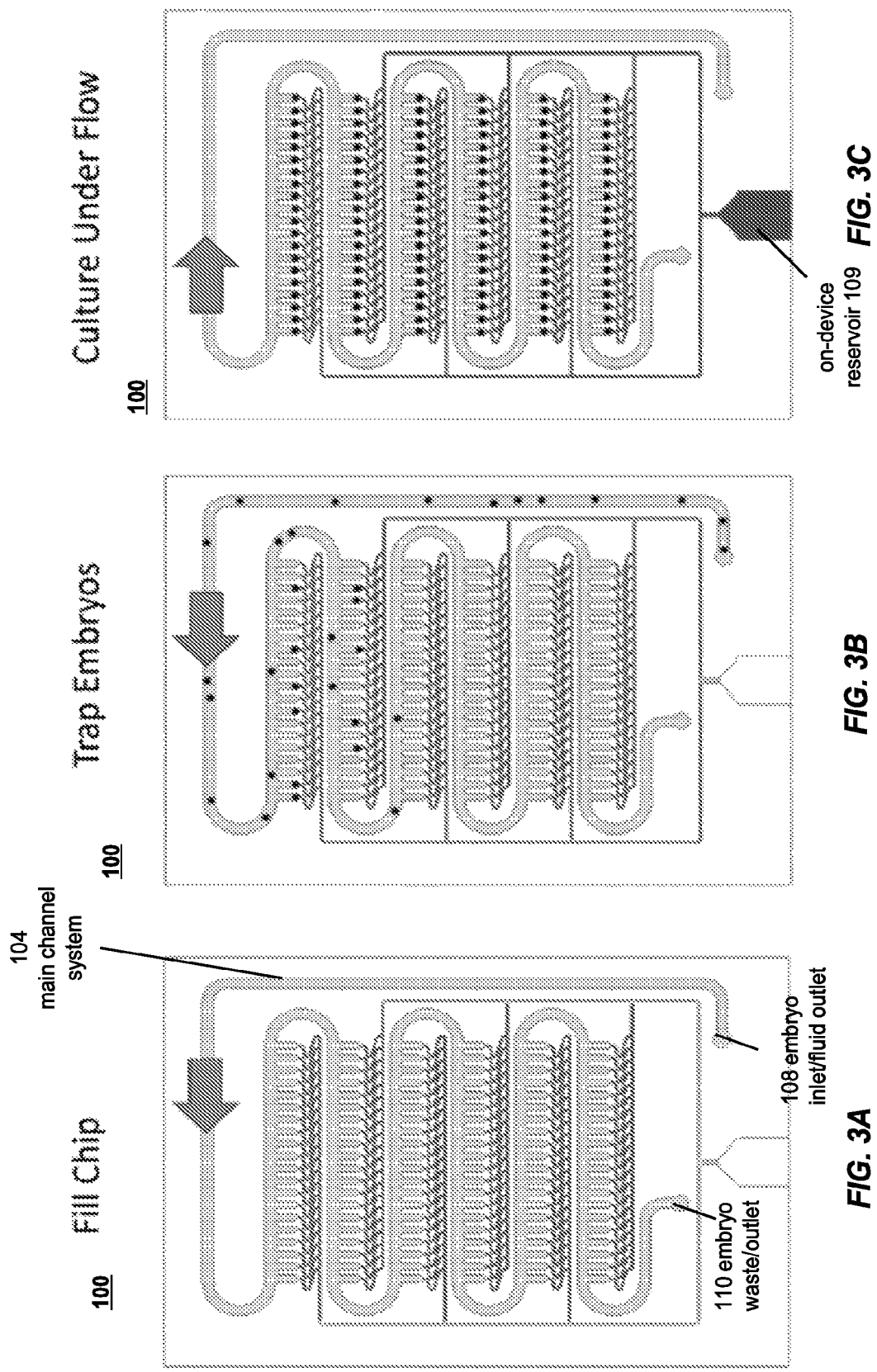
FIGS. 3A-3C are schematic diagrams showing a front view or top view of a microfluidic device according to one embodiment described herein during operation.
Figure 4:
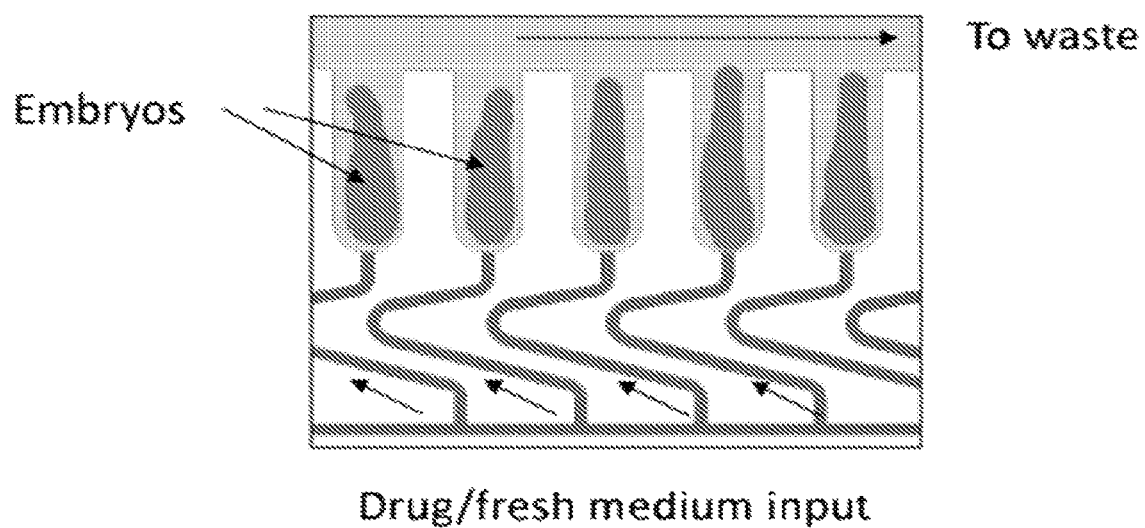
FIG. 4 is a schematic diagram showing embryos received in their respective chambers after 3-7 days of culture. In one embodiment, the chambers are geometrically sized to allow embryos growing in a limited number of orientations in order to facilitate imaging without further manipulation. The embryos receive fresh medium (with or without a test agent such as drug) supplied by the connecting channels through the medium opening, while the waste or conditioned medium derived from the embryos are carried away by a fluid flowing across the channel openings of the chambers.

In some embodiments, e.g., where the microfluidic device described herein is operated in an upright position, the reservoir can be located on the top portion of the device during operation, e.g., as shown in FIG. 1. However, the reservoir can also be located at other positions, e.g., on the side(s), or at the bottom portion of the device during operation, e.g., as shown in FIGS. 3A-3C. In other embodiments, the reservoir can be placed off of the microfluidic devices described herein, for example, when a larger volume is needed but cannot be accommodated on the devices.

The connecting channels 124 are adapted to distribute a fluid received by the medium inlet(s) to the corresponding chambers 114 through the medium opening 120 of the corresponding chambers 114. The fluid (e.g., a culture medium with or without a test agent or molecule) can flow past the target biological specimen in the corresponding chamber so as to place a force thereon that is counteracted by the force of gravity on the target biological specimen. Depending on the complexity of the microfluidic device design, including, e.g., the total number and locations of the medium inlet(s) 122 and the corresponding set of chambers to which each fluid received by the medium inlet(s) flow, the medium-manifold system can comprise a fluidic network to facilitate distribution of a fluid received by the medium inlet(s) to the appropriate connecting channels and thus the corresponding chambers 114 through the medium opening 120 of the corresponding chambers 114.

By way of example only, FIG. 1 shows a medium-manifold system 106 comprising a medium inlet 122, a main medium distribution network 116, and a plurality of connecting channels 124 connecting between the corresponding medium openings 120 and a distribution segment of the main medium distribution network 116. As shown in FIG. 1, the main medium distribution network 116 is fluidly connected to at least one medium inlet 122 and comprises a plurality of distribution segments 116-*n* (e.g., 116-1 representing a first distribution segment; 116-2 representing a second distribution segment), wherein each of the distribution segments 116-*n* fluidly connects to a plurality of connecting channels 124. Each of the distribution segments can be fluidly connected to the same medium inlet or a subset of the distribution segments can be fluidly connected to a different medium inlet. For example, the main medium distribution network 116 as shown in FIG. 1 distributes a fluid received by a single medium inlet 122 to a plurality of chambers 114 arranged in multiple (e.g., at least two or more, including, e.g., at least 3, at least 4, at least 5 or more) linear or ordered arrays. Each array of the chambers is supported by a corresponding distribution segment, and all the distribution segments are fluidly connected to a main medium channel of the main medium distribution network 116. In this example, a medium inlet can be used to introduce a fluid into all of the chambers. In some embodiments, the main medium distribution network can be subdivided to supply only a subset of target biological specimens with a given test agent or molecule.

Figure 5:
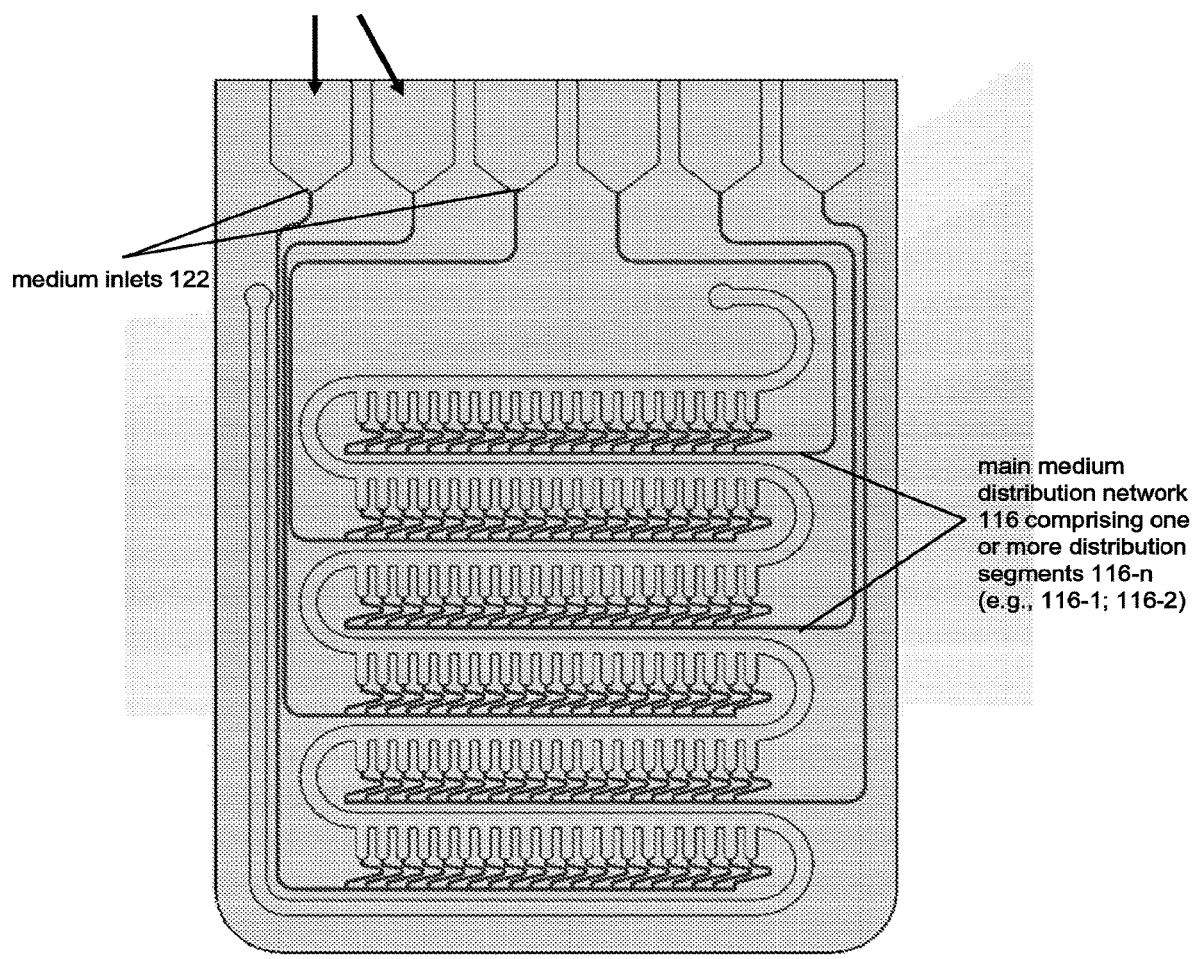
FIG. 5 is a schematic diagram showing a front view or top view of a microfluidic device according to one embodiment described herein with multiple medium inlets. In some embodiments, each medium inlet can be fluidly connected to a distinct reservoir, which can be either placed on the device or separated from the device.

The main medium distribution network can be modified to provide multiple fluidly independent conditions in a single microfluidic device described herein (e.g., to supply different fluids or test agents or molecules to different subsets of the chambers 114 in a single microfluidic device), while allowing for the same configuration of the main channel system for use in separating target biological specimens into individual chambers and/or in carrying away secretion and/or waste from the target biological specimens within the chambers. For example, more than one medium inlets, each designed to supply a different fluid (e.g., each fluid comprising a different test agent or molecule) to only a subset of the chambers 114, can be created; and each medium inlet can be fluidly connected to the corresponding subset of the chambers 114 through a separate main medium distribution network. FIG. 5 illustrates an embodiment of a microfluidic device with multiple medium inlets 122. As shown in FIG. 5, the six medium inlets 122 are fluidly connected to six distinct distribution segments 116-*n*, wherein each distribution segment 116-*n* is fluidly connected to a distinct subset of the chambers 114. Not only can this design permits parallel or simultaneous testing of different test conditions in a single device, but it can also permit duplicate samples for each test condition. While FIG. 5 shows multiple reservoirs each corresponding to a distinct medium inlet, it should be noted that the reservoirs can be placed on the device or off the device. In some embodiments, the number of reservoirs can vary with the need and requirements (e.g., volume) of an application, and/or device size.

Accordingly, in some embodiments of this aspect and other aspects described herein, the medium-manifold system can comprise a first set of the connecting channels and a second set of the connecting channels. In some embodiments, the first set and the second set can fluidly connect to the same medium inlet for receiving the same fluid (e.g., a culture medium with or without a test agent or molecule). In other embodiments, the first set can fluidly connect to a first medium inlet for receiving a first fluid, while the second set can fluidly connect to a second medium inlet for receiving a second fluid, wherein the composition of the second fluid is different from the first fluid. For example, the first and the second fluid can comprise different test agents or molecules, or the same agent in different concentrations. The first and second set of the connecting channels can each connect to a different main medium distribution network. Each of the main medium distribution networks can comprise a first distribution segment and optionally a second distribution segment.

The medium-manifold system 106 of the microfluidic devices described herein does not require a separate medium outlet. After the fluid flows into the chamber 114 via the medium opening 120 of the corresponding chamber 114 and contacts the target biological specimen therein, the "exposed" fluid is then carried away by a fluid flowing across the chambers in the channel segment(s) 112-*n* of the central portion 112-*n* between the inlet 108 and the outlet 110. As described earlier, the central portion 112 is not only used to flow a fluid comprising target biological specimens for separation of the target biological specimens into individual chambers, but is also used to allow a fluid, e.g., a culture medium, flowing across in order to carry away secretion and/or waste from the target biological specimens, which can be either discarded or collected as a sample for analysis.

As shown in FIG. 1, the connecting channels 124 (connecting between the corresponding medium openings 120 and a segment of the main medium distribution network 116) are curved so as to provide a compact yet high-resistance flow channel to balance out the fresh fluid input from the channel segment above the chamber and/or to facilitate separation of target biological specimens into individual chambers, and also to reduce bubble formation. However, other shapes of the connecting channels (e.g., linear connecting channels or connecting channels with other curve paths) can also be used provided that bubble removal is not significantly impeded.

The resistance of the connecting channels 124 can be determined empirically. Without wishing to be bound by theory, one can design a connecting channel to have a resistance flow to be somewhat low to provide significant fluid flow during trapping of target biological specimens (e.g., embryos), which will then dramatically increase resistance and shift flow to the next chamber(s). A high resistance flow in the connecting channels 124 (e.g., more than 10-100× resistance flow of the channel segments 112-*n* above the channel openings 118 of the chambers 114) may cause inefficient trapping by diverting most of the target biological specimens (e.g., embryos) into the channel segments 112-*n*. Additionally, too large connecting channels 124 can also cause a large dead volume in the system and possibly poor uniformity of dosing when culturing the target biological specimens (e.g., embryos) after reversing flow since high resistance in the connecting channels 124 improves fluid flow uniformity.

In some embodiments of this aspect and other aspects described herein, a surface of the main channel system 104 and/or the medium-manifold system 106 in contact with a fluid can be modified for reducing non-specific binding of an entity (e.g., a biological specimen and/or a test agent or molecule) in a fluid to the surface of the main channel system and/or the medium-manifold system. For example, the surface of the main channel system 104 and/or the medium-manifold system 106 in contact with a fluid can be coated with a surfactant, e.g., PLURONIC® 127, or a blocking protein such as bovine serum albumin, for reducing cell or protein adhesion thereto. Additional surfactant that can be used to reduce the adhesive force between the surface of the main channel system 104 and/or the medium-manifold system 106 and non-specific binding of an entity (e.g., a biological specimen and/or a test agent or molecule) in a fluid include, but are not limited to, hydrophilic (especially amphipathic) polymers and polymeric surface-acting agents;

non-ionic agents such as polyhydric alcohol-type surfactants, e.g., fatty acid esters of glycerol, pentaerythritol, sorbitol, sorbitan, and more hydrophilic agents made by their alkoxylation, including polysorbates (TWEEN®); polyethylene glycol-type surfactants such as PLURONIC surfactants (e.g., poloxamers), polyethylene glycol (PEG), methoxypolyethylene glycol (MPEG), polyacrylic acid, polyglycosides, soluble polysaccharides, dextrins, microdextrins, gums, and agar; ionic agents, including anionic surfactants such as salts of carboxylic acids (soaps), sulfuric acids, sulfuric esters of higher alcohols; cationic surfactants such as salts of alkylamine type, quaternary ammonium salts, or amphoteric surfactants such as amino acid type surfactants and betaine type surfactants. A skilled artisan will readily be able to determine appropriate methods and/or reagents for use to reduce non-specific binding of an entity (e.g., a biological specimen and/or a test agent or molecule) in a fluid to the surface of the main channel system 104 and/or the medium-manifold system 106, based on the substrate material of the microfluidic devices and/or types of entities to be blocked.

In some embodiments of various aspects described herein, the microfluidic device can further comprise at least one or more gradient generators fluidly connected upstream of the connecting channels and/or distribution segments described herein. By fluidly connecting a gradient generator upstream of the connecting channels and/or distribution segments described herein, a fluid (e.g., a culture medium with a test agent or molecule) supplied by a reservoir can be diluted to a desired concentration prior to delivery to the target biological specimens in the chambers. In some embodiments where at least two or more gradient generators are used, each or subsets of the target biological specimens can be exposed to different concentrations of one or more test agents, even when the connecting channels are all fluidly connected to the same medium inlet(s). In some embodiments, the gradient generator(s) can be integrated into the microfluidic device. In such embodiments, the gradient generator(s) can be located between the medium inlet(s) and the connecting channels. In other embodiments, the gradient generator can be provided in a separate device (e.g., external to the microfluidic device described herein) and fluidly connected to the medium inlet of the microfluidic device described herein.

In some embodiments, any gradient generator known in the art can be incorporated downstream (e.g., immediately downstream) of the reservoir(s) to provide a gradient of an agent or an agent mixture to be delivered. This is an example way to rapidly generate dilution curves, so that each chamber or each subset of chambers can receive the agent or agent mixture at a uniform, but different concentration.

In some embodiments, a gradient can be formed across each chamber by having two or more medium openings fluidly connected to two or more different reservoirs, respectively, to deliver an agent or an agent mixture into each chamber, each at a different concentration. This can be accomplished by having at least some of the distribution and/or connecting channels be in a separate fluidic layer given the need to cross fluidic paths when multiple chambers are involved.

As used herein, the term "gradient generator" refers to a structural microfluidic element that generates a concentration gradient in a fluidic channel. Generating various types of microfluidic concentration gradient generators, including, e.g., pressure-driven gradient generators, and/or convection and/or diffusion-based gradient generators, are known in the art. Example of such gradient generator design include, but are not limited to "Christmas tree" mixer network, T-junction, Y-junction and flow splitters, pressure balance, and/or hydrogel/extracellular matrix. Additional information about microfluidic gradient generator can be found, e.g., Toh et al. "Engineering microfluidic concentration gradient generators for biological applications." Microfluidics and Nanofluidics (2013) 16 (1-2): 1-18, the content of which is incorporated herein by reference in its entirety.

In some embodiments of various aspects described herein, the microfluidic device can further comprise an optically transparent cover. The optically transparent cover can provide sealing and/or a closure for the fluidic paths disposed in a surface of the main body of the microfluidic devices described herein. Thus, in some embodiments, the optically transparent cover and the main body can define the main channel system and the medium-manifold system described herein. By the term "optically transparent" as used herein is meant an object having a transmittance of at least about 50% (including, at least about 60%, at least about 70%, at least about 80%, at least about 90%, at least about 95%, at least about 98%, or up to 100%) at a wavelength in the visible spectrum (e.g., 380 nM-780 nM). Examples of an optically transparent material that can be used as in an optically transparent cover include, e.g., but are not limited to, silicones, PDMS, cellulose, fluorinated polymers (e.g., non-porous clear films such as DAI-EN from Daikin). If oxygen is desired to be delivered through the body of the device or other means, non-permeable sealing membranes/films made from any thermoplastic or thermoset with desired optical properties can be used. Adhesion can be be provided by pressure-sensitive adhesive, solvent bonding, welding, etc.

In some embodiments, the optically transparent cover can be adapted to be gas-permeable. For example, the optically transparent cover can be thin enough to be gas-permeable or made from a gas-permeable material. In one embodiment, the optically transparent cover can be a gas-permeable and/or liquid-impermeable sealing membrane. In one embodiment, the optically transparent cover can be approximately 50 μm thick. While the thickness of the optically transparent cover can affect the gas permeability, material selection can be typically more important.

In some embodiments, the optically transparent cover can be pierced, e.g., by a pipette or needle, to permit access of the target biological specimens.

Depending on types of the target biological specimen and/or measurements to be taken, different sensing devices can be incorporated into the chambers of the microfluidic devices described herein. For example, in some embodiments, the microfluidic device can further comprise at least one electrode in at least one or a plurality of (e.g., at least two or more) the chambers. In some embodiments, the microfluidic device can further comprise two electrodes in at least one or a plurality of (e.g., at least two or more) the chambers. The electrodes disposed in the chamber(s) can provide electrical readings and thus enable measurement of cell activity that induces a change in the electrical readings, e.g., contractile activity of muscle cells and/or tissue (muscle activity), contractile activity of heart cells and/or tissue (heart beat), and/or activity of brain cells and/or tissue (e.g., equivalent to electroencephalogram (EEG) and/or myography). Additionally or alternatively, the electrodes can be used to provide a current to the target biological specimens within the chambers. In some embodiments, the electrodes can be used to provide a current to contract cells, e.g., muscle cells and/or tissue. In some embodiments, the electrodes can be used to provide a current to stimulate target biological specimens, e.g., small living organisms, to turn over or move at a certain time point for more complete imaging purpose.

In some embodiments, oxygen sensors can be incorporated into the chambers of the microfluidic devices described herein. In some embodiments, optode sensors, e.g., for ratiometic sodium imaging or other physiological condition monitoring, can be incorporated into the chambers of the microfluidic devices described herein. An exemplary optode nanosensor as described in Ruckh et al., Sci Rep. (2013) 3:3366 or in Balaconis et al., Anal Chem (2012) 84:5787-93 can be used herein.

In some embodiments, electric and/or electrochemical sensors can be incorporated into the chambers of the microfluidic devices described herein. Examples of such sensors include, but are not limited to electrochemical sensors disclosed in U.S. Prov. App. No. 62/200,454 filed Aug. 3, 2015, the content of which is incorporated herein by reference in its entirety.

In some embodiments, pH and/or CO2 optical sensors, e.g., as produced by PreSens Precision Sensing GmbH, can be incorporated into the chambers of the microfluidic devices described herein.

In some embodiments, the microfluidic devices described herein can be adapted for multiplexed diagnostics that require many single samples but many shared reagents or a single sample analyzed many different ways. For example, the microfluidic devices described herein can be used for ELISAs. Samples can be loaded into the chambers, either by pipetting or by having proteins captured onto encoded beads and flowed into the chambers, in a similar manner for target biological specimens (e.g., embryos). Then, the connecting channels 124 can be used to deliver to the samples in the chambers various labeling antibodies, labels/enzyme substrates, calibration standards, and other reagents, followed by an optical readout.

In one embodiment, the microfluidic devices described herein can be in the same format as a standard well plate: ~127 mm by 85 mm. The number of the chambers 114 can be about 100-200 per device (e.g., about 120 chambers per device) but can be fewer or more, depending on user's applications. For example, organoid trapping can take up far less space per organoid than trapping embryos, allowing easily scaling up by 10×-100× per device. The dimensions of each chamber can be 1.75 mm×1.75 mm×5 mm.

Exemplary Systems Comprising a Microfluidic Device Described Herein

A system for high through-put cell culture and/or assay/analysis is also provided herein. The system comprises: (a) a plurality of the microfluidic devices according to one or more embodiments of various aspects described herein; (b) a plurality of holders, each of the plurality of holders configured to hold a single microfluidic device; and (c) a fluid handling module to control fluid flow in the main channel system and the medium-manifold system.

Figure 2A:
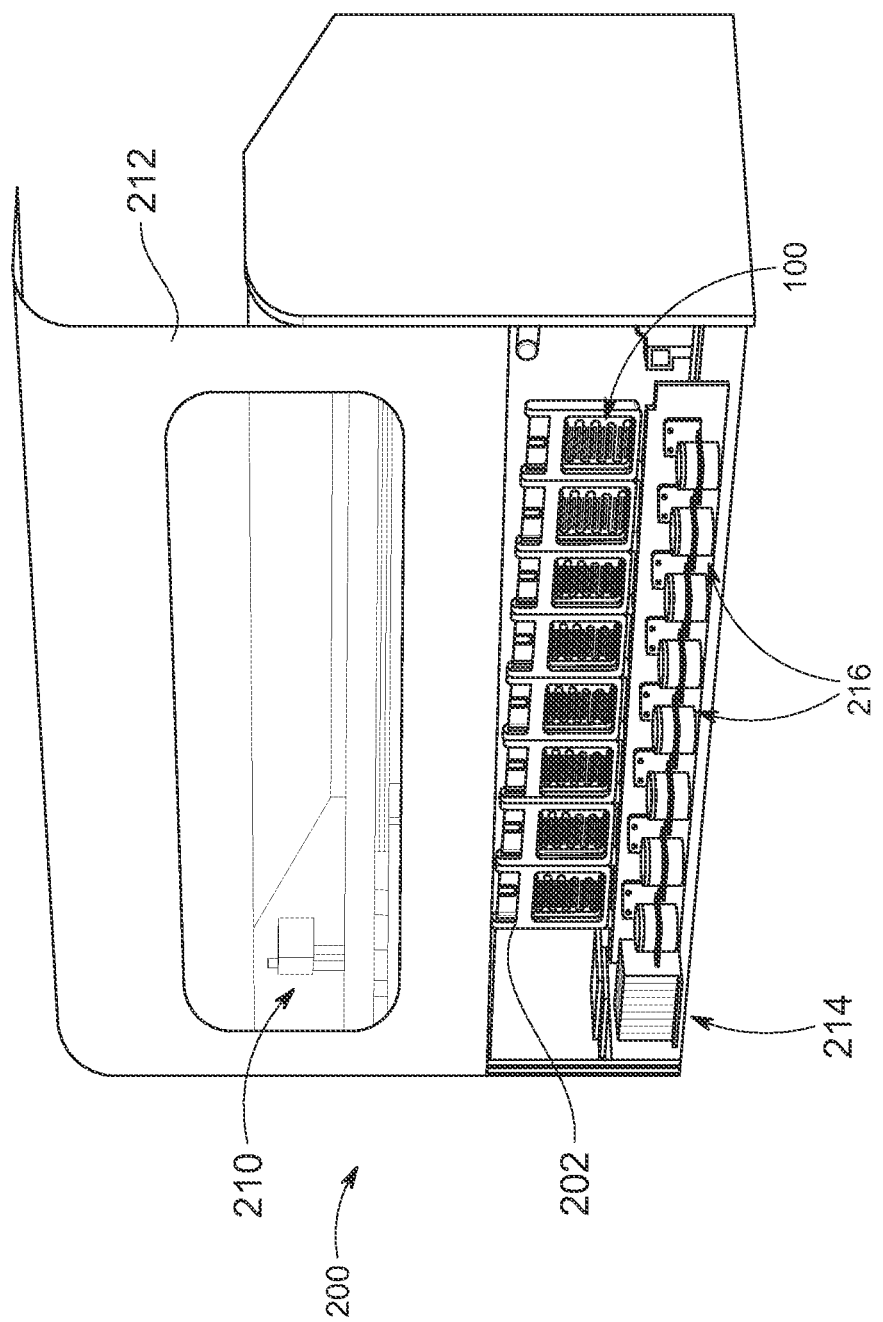
FIGS. 2A-2B are schematic diagram showing various perspective views of a system for high-throughput culture and screening of target biological specimens, e.g., embryos, according to one embodiment described herein.

FIG. 2A illustrates one embodiment of a system described herein. The system 200 comprises at least two or more (including, e.g., at least three, at least four, at least five, at least six, at least seven, at least eight, at least nine, at least ten or more) of the microfluidic devices 100 described herein. Each of the microfluidic devices 100 is inserted in a corresponding holder 202 such that the channel openings 118 are located below the channel segments 112-n in the direction of gravity during operation of the microfluidic devices.

Figure 2B:
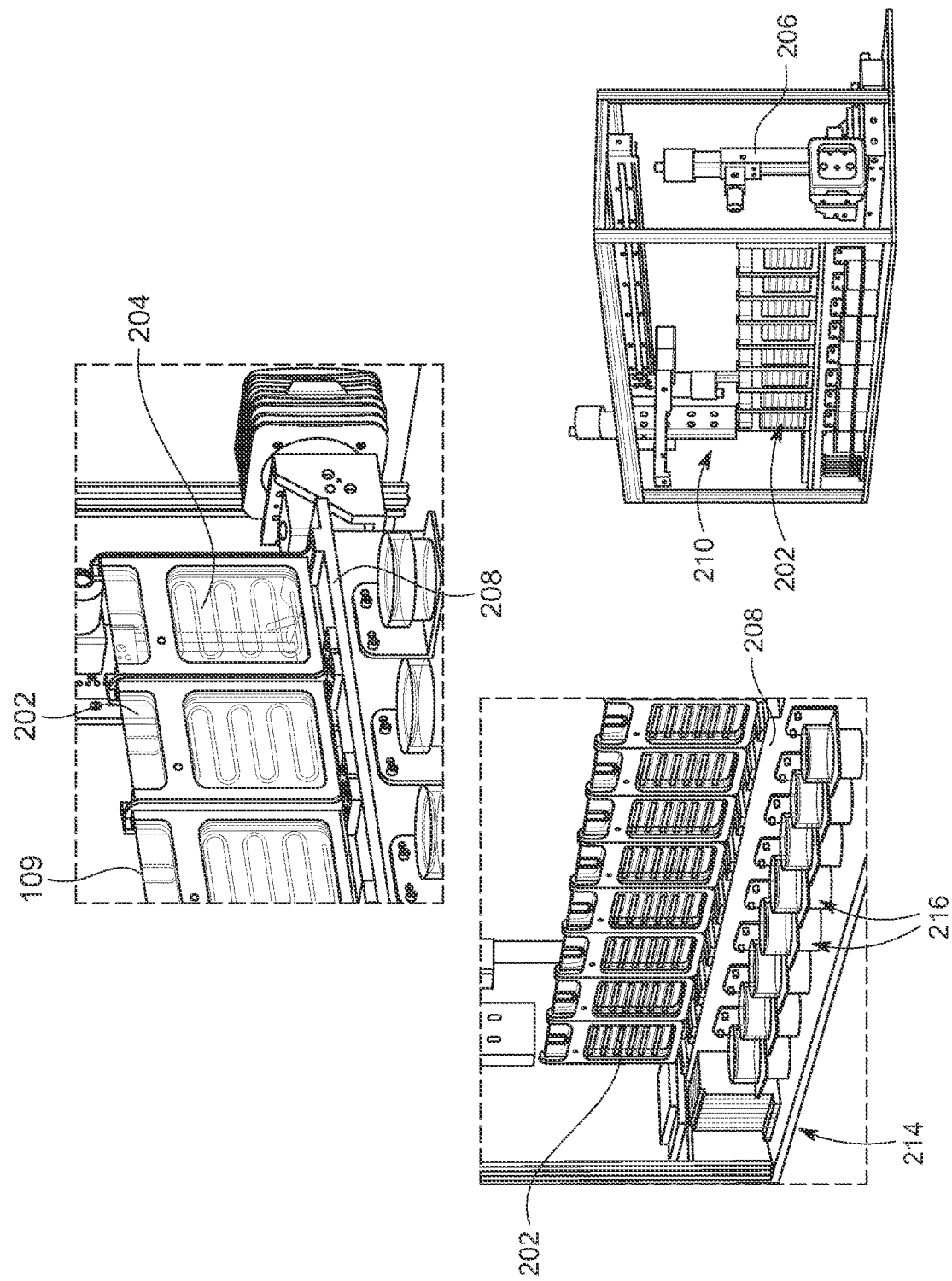

The inventors have discovered that, in one embodiment, vertical positioning of the microfluidic devices during operation provides optical and fluid handling access while stably maintaining the embryos in individual compartments in place (e.g., even with fluid flow) by gravity. Accordingly, in one embodiment, the holder can be configured to hold a microfluidic device in an upright direction that is parallel to the direction of gravity, e.g., as shown in FIGS. 2A-2B. Vertical positioning of the microfluidic devices described herein during operation can improve handling, as compared to horizontal systems, by minimizing the need to reach or manipulate the microfluidic device, thus reducing risk of contamination. Vertical positioning of the microfluidic devices described herein during operation can also allow the holders and related instruments such as a microscope to be cleaned more effectively, as compared to horizontal systems with optics under or below the holders. However, in some embodiments, the microfluidic devices can be positioned at an angle of about 45 degrees relative to the direction of gravity (e.g., between −45 degrees and +45 degrees from a vertical axis along the direction of gravity). In some embodiments, the microfluidic devices can be placed parallel to the ground (e.g., 0 degree or 180 degrees) if needed. This would, however, reduce the stability of target biological specimens disposed in the chambers.

As used herein, the term "holder" denotes a construction or an apparatus that can hold a microfluidic device according to one or more embodiments described herein. The holder can be designed to suit the need of different applications, e.g., "plug and play" function and/or imaging purpose. For example, as shown in FIG. 2B, a holder 202 can comprise a viewing window 204 for viewing at least one or more (e.g., some or all) target biological specimens in the chambers. In some embodiments, a holder 202 can comprise a docking interface bearing one or more fluidic connectors configured to matingly and removably engage corresponding fluidic ports on the corresponding microfluidic device 100 when the microfluidic device is loaded into the docking interface. Thus, the microfluidic devices can be quickly set up for culture and/or analysis as soon as they are loaded into the holders. For example, a user does not have to connect fluidic tubing directly to the ports of the microfluidic device every time when he/she sets up a new culture and/or assay in a new microfluidic device described herein.

Although the holders 202 are illustrated to be mounted on a platform 208, which can be driven by one or more actuators (including, e.g., any conventional mechanical actuators, hydraulic actuators, electro-mechanical actuators, linear motors, linear actuators, rotary actuators, belt actuators, and/or chain actuators) along one or more axes, the holders can comprise one or more motor(s), gear(s), actuators to enable translational movement of the holders relative to a detection module such as a microscope 206. In these embodiments, the holders 202 can be independently disposed to translate along one or more axes (e.g., X, Y, Z), e.g., relative to a detection module such as a microscope 206. The translation of the holders along one or more axes (e.g., X, Y, Z) can be actuated by any conventional mechanical actuators, hydraulic actuators, electro-mechanical actuators, linear motors, linear actuators, rotary actuators, belt actuators, and/or chain actuators. This can allow the microscope, even if the microscope is fixed at one location, to have optical assess to each chamber of the microfluidic device(s) 100 when desirable. For example, the system can further comprise at least one rail or a conveyor belt along which at least one of the plurality of holders is disposed to translate.

In some embodiments, the holders 202 can be detachable from the platform 208. In these embodiments, the microfluidic device described herein 100 can be engageably disposed in the detachable holder as an integral unit. When in use, the holder 202 (together with the microfluidic device 100) can be mounted onto the platform. The holder 202 can move along a conveyor belt and have a smaller 3-axis (e.g., X, Y, Z) stage for imaging.

While FIGS. 2A-2B show a system comprising a single row of the microfluidic devices disposed in respective holders, the system, in some embodiments, can comprise multiple rows (e.g., at least two or more rows) of the microfluidic devices disposed in respective holders. The fluid handling module or fluid handling robot can be fluidly connected to each of the microfluidic devices described herein.

The system 200 can be housed in an enclosure 212, e.g., a temperature-controlled and/or carbon dioxide-controlled incubator. In the enclosure, the target biological specimens present in the chambers can be maintained and/or grown under a physiological cell culture condition.

The system 200 also comprises a fluid handling module. The fluid handling module of the system is designed to control fluid flow rate and/or direction in the main channel system and the medium-manifold system of the microfluidic device(s) described herein during operation. In some embodiments, the fluid handling module can comprise a pump system. For example, the pump system can be configured to drive culture medium from a reservoir to supply nutrients to target biological specimen in the chambers through the connecting channels. The reservoir can be integrated or external to the microfluidic device. In some embodiments, the pump system can be configured to drive a fluid through the connecting channels at a flow rate sufficient to remove the embryo from the respective chambers. Pump systems for control of fluid delivery are known in the art and can be adapted in the system described herein. Examples of a pump system include, but are not limited to, a vacuum-driven system, a pressure-driven system, a peristaltic pump, a pneumatic pump, a mechanical pump, an acoustofluidic pump, an electrofluidic pump, and a combination of two or more thereof.

In some embodiments, a vacuum-driven system can be used to provide suction of a culture medium (with or without a test agent or molecule) from a reservoir integrated into the microfluidic device described herein across the target biological specimens present in the chambers. In these embodiments, each target biological specimen can receive fresh fluid not contacted by other target biological specimens. This is particularly useful to achieve robust analysis of response of the target biological specimens (e.g., embryos) to an infectious agent (e.g., pathogens) where a large number of the target biological specimens (e.g., embryos) contacted with the infectious agent (e.g., pathogens) can be in the process of dying. In addition, the vacuum-driven system can also provide additional safety measure for handling of an infectious agent by reducing the risk of spills and/or aerosol formation. An automated fluid handling robot can also be included to provide fluid transfer capability for pathogen infection and compound screening.

In one embodiment, as shown in FIGS. 2A-2B, a vacuum regulator 214, including, e.g., an electronically controlled regulator where an electrical voltage or frequency or other signal controls the output pressure using an internal pressure sensor, can be used to drive a fluid by connecting to a collection reservoir 216 that acts as a vacuum chamber. Fluid flows through the microfluidic device 100, through the device ports, through tubing, and into the collection reservoir 216, with the outgoing air being protected by a filter or secondary fluid trap. Alternatively, a peristaltic pump, electroosmotic pump, syringe pump, or other means of actuation can be utilized for the same purpose. To avoid leakage of sample or reagent materials (e.g., biohazardous materials) from the fluidic system, in some embodiments, negative pressures or pumps can be used at the outlet.

In some embodiments, the system can further comprise a detection module. While the microscope 206 is shown as an example of the detection module in FIG. 2B being positioned parallel to the holders for imaging of microfluidic devices that are positioned vertically, any detection module capable of performing any method of detection disclosed herein or other methods known in the art can be used. For example, in addition to or other than assaying on or imaging target biological specimens within their respective chambers, the output fluid from the microfluidic device can also be used for alternative readouts of the condition of the target biological specimens disposed in the respective chambers. In some embodiments, the detection module can include a sample-treatment module before the sample is detected for analysis. For example, the sample including or derived from the biological specimen present in the chamber(s) can be subjected to immunostaining before detection by microscopy, or be subjected to RNA/protein isolation before detected by PCR or microarrays. Examples of the detection module can include, without limitations, a microscope (e.g., a brightfield microscope, a fluorescence microscope, or a confocal microscope), a spectrophotometer (e.g., UV-Vis spectrophotometer), a cell counter, a biocavity laser (see, e.g., Gourley et al., J. Phys. D: Appl. Phys. 36: R228-R239 (2003)), a mass spectrometer, a PCR device, an RT-PCR device, a cell culture platform, a microarray, an imaging system, a RNA, DNA and/or protein isolation/purification device, an affinity column, a particle sorter, e.g., a fluorescent activated cell sorter, capillary electrophoresis, a sample storage device, and sample preparation device.

In some embodiments, the detection module can comprise an imaging device. Non-limiting examples of the imaging device include brightfield, darkfield, phase-contrast, epifluorescence, fluorescence, microfluorimetry, confocal, multiproton excitation microscopy, and a combination of two or more thereof. In one embodiment, the imaging device can comprise a microscopic blade as described in the International Patent Application No. WO 2014/210339, the content of which is incorporated herein by reference in its entirety. In some embodiments, the imaging device can be movably disposed along one or more axes, one of which is parallel to an axis along which the holders are disposed. The capability of the imaging device to move along one or more axes during imaging can enable automated analysis of a large number of target biological entities without further manipulation.

In some embodiments, a computer system can be connected to the detection module, e.g., to facilitate the process of sample treatment, detection and/or analysis.

In some embodiments, the system can be configured to provide full culture capabilities of target biological specimens (e.g., embryos) including, e.g., but not limited to medium exchange/perfusion, pH, temperature, and/or medium quality logging and maintenance. For example, in some embodiments, where the system is configured for *Xenopus* culture, the system can be configured to comprise a reservoir that provides sufficient space for *Xenopus* embryos to hatch and swim. The above analytics can be accomplished, for example, by integrating sensor modules in the flow path of the fluid or even integrated into each culture chamber (e.g., pH or oxygen sensitive dyes can be infused into polymers and sensed optically using an imaging system). Conductivity, pH, temperature and other information can be connected to the system controls for logging. Additionally or alternatively, some of this information can be collected by imaging when image-based sensors are used (e.g., but not limited to PreSens pH, CO2, or O2 sensor films).

In some embodiments, the system can further comprise a robotic structure 210 (e.g., a robotic arm) for interfacing with the microfluidic device for a specific purpose. For example, in one embodiment, the robotic structure 210 can be configured for assessing or recovering a target biological specimen from the chambers. In these embodiments, the robotic structure can be configured to create an aperture in the optically transparent cover over a chamber such that the target biological specimen received in the corresponding chamber can be removed therefrom through the aperture. Alternatively or additionally, the robotic structure can be configured to collect a sample from the microfluidic device(s), and/or replenishing an on-device reservoir with fresh culture medium. The robotic structure can be actuated to translate along one or more axes (e.g., X, Y, Z), e.g., relative to the holders described herein.

In some embodiments, the system described herein can be controlled by a user-friendly web application that can provide remote control of the system and experimental design. Output signals or results from the detection module can be integrated with a processing software for automated analysis of the biological specimens, e.g., in response to a test agent or molecule. In some embodiments, output images from an imaging device can be integrated with image processing software for automated analysis of the biological specimens, e.g., in response to a test agent or molecule.

In some embodiments, the system described herein can be adapted to be a high-throughput system that allows screening of about 1000-2000 embryos per experiment (e.g., 3-7 days) to identify susceptible, resistant, and tolerant embryos, and/or to screen ion channel drugs (and other libraries) on the embryos to identify agents that confer optimal tolerance. For example, the system can comprise a plurality of microfluidic devices according to one or more embodiments described herein, each of which is configured to rapidly separate about 100-300 embryos into ordered, indexed arrays of chambers. The chambers can be sized to geometrically constrain the embryos after growth over a period of time (e.g., 3-7 days) for optimal imaging. In some embodiments, at least about 8 microfluidic devices or more can be loaded into their respective holders, e.g., in a "plug and play" manner, to permit automated fluid handling and imaging instrument for parallel culture and continuous imaging. The system can perform simplified and automated fluidic handling for embryo culture and pathogen infection. The system can also enable robust pathogen containment at the microfluidic device, fluid handling, and whole-instrument levels by sealing the fluidic path, using vacuum to drive the flow, and having a gas-permeable sealing membrane. Additionally, the system can provide optical access for automated imaging using both brightfield and fluorescence modalities.

Figure 6A:
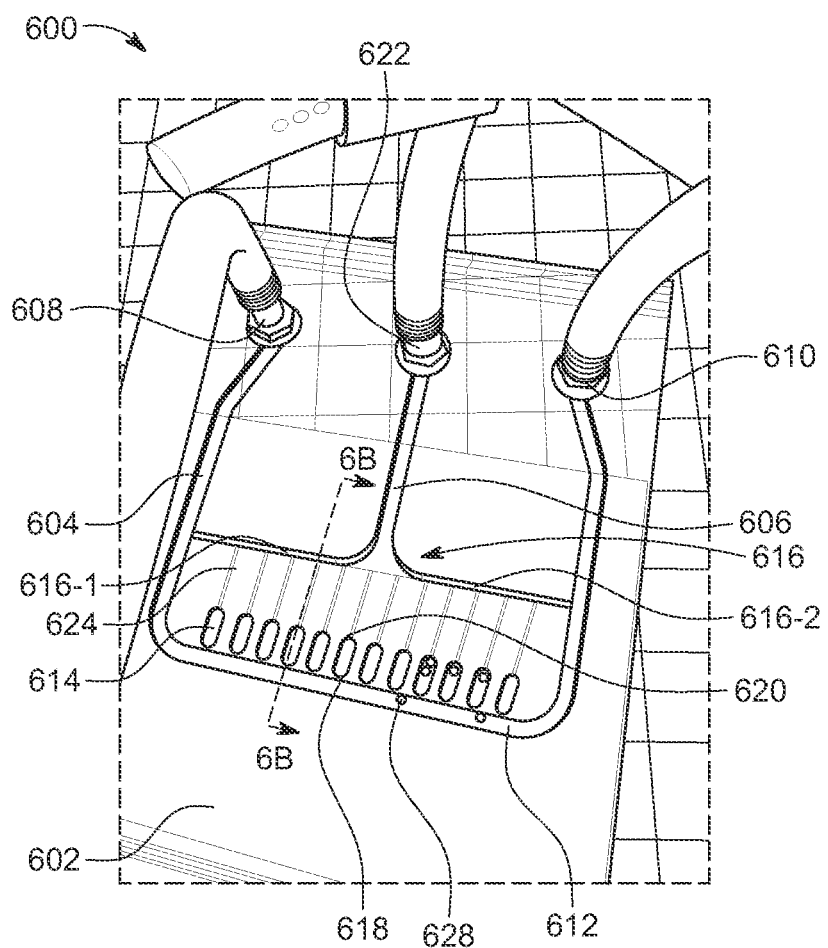
FIG. 6A is a schematic diagram showing a front view or top view of a microfluidic device according to another embodiment described herein for high-throughput cell culture.

Referring now to FIG. 6A, one embodiment of another microfluidic device according to aspects of the present disclosure is illustrated. A microfluidic device according to aspects of the present disclosure can have different geometries, layouts and configurations than those described above and illustrated in FIGS. 1-5. FIG. 6A shows such a microfluidic device 600.

Similar to the microfluidic device 100, the microfluidic device 600 includes a main body 602, a main channel system 604 and a medium-manifold system 606 disposed therein.

The main channel system 604 is configured to provide a fluidic passageway for separating a plurality of target biological specimens 628 into individual chambers 614. The medium-manifold system 606 is configured to provide a fluidic passageway for supplying a fluid (e.g., a culture medium optionally comprising a test agent) to individual target biological specimens 628. The main body 602, the main channel system 604 and the medium-manifold system 606 are identical to the main body 102, the main channel system 104 and the medium-manifold system 106, except for the different layout, as shown and disclosed below.

In particular, the main channel system 604 has an inlet 608, an outlet 610, a central portion 612 located between the inlet 608 and the outlet 610, and a plurality of chambers 614 extending transversely to a single channel segment 612 from channel openings 618. As described above, microfluidic devices according to aspects of the present disclosure can include at least one or a plurality (e.g., at least two or more) of channel segments and, in the case of the microfluidic device 600, the microfluidic device 600 has the one channel segment 612.

Similarly, the medium-manifold system 606 includes a medium inlet 622, a main medium distribution network 616, and a plurality of connecting channels 624 connecting between the corresponding medium openings 620 and a pair of distribution segments 616-1 and 616-2 of the main medium distribution network 616. The main medium distribution network 616 distributes a fluid received by the medium inlet 622 to the plurality of chambers 614 arranged in the single linear or ordered array. Although described as a pair of distribution segments 616-1 and 616-2, which diverge from each other within the main medium distribution network 616, the distribution segments 616-1 and 616-2 alternatively can be considered a single distribution segment that corresponds with the single channel segment 612 of the main channel system 604.

As shown based on the microfluidic device 100 compared to the microfluidic device 600, the geometries of the microfluidic devices disclosed herein can vary without departing from the spirit and scope of the present disclosure. Such variations include, for example, the number of channel segments, the number of distribution segments, the number of chambers for each channel and distribution segment, and the like. The number of channel segments, distribution segments and chambers can vary depending on, for example, the number of biological specimens a microfluidic device is configured to support. Fewer channel segments, distribution segments and/or chambers provide for more simplified geometries of the microfluidic devices.

Figure 6B:
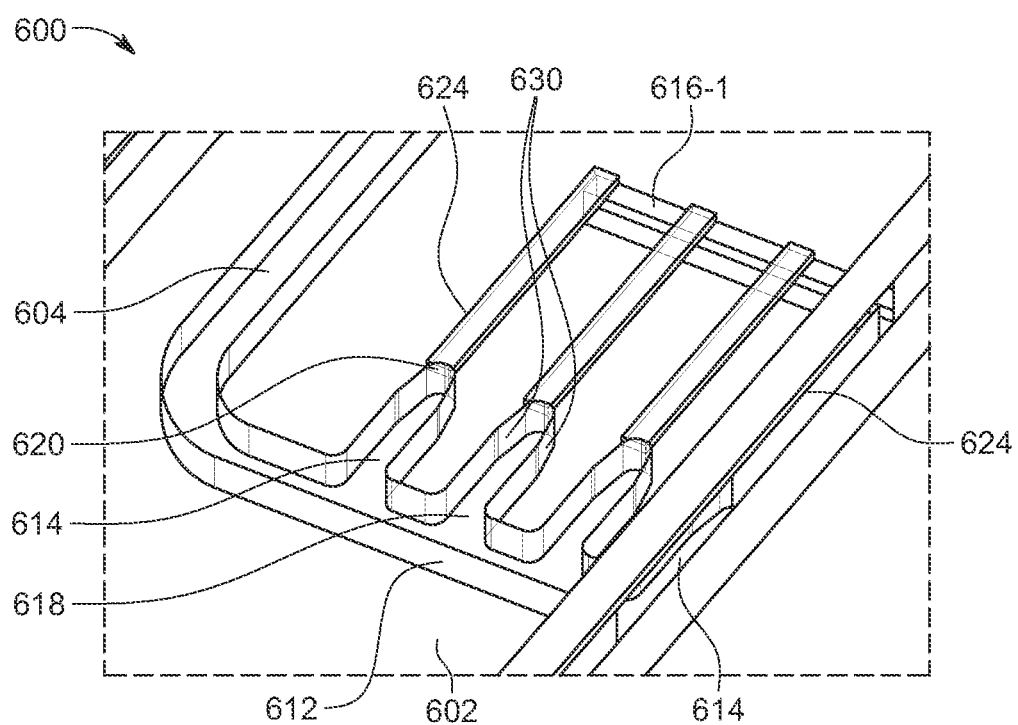
FIG. 6B is a schematic diagram showing a partial front view or top view of the microfluidic device of FIG. 6A, with a cross-section view along the line 6B-6B in FIG. 6A.

Referring to FIG. 6B, the varying geometries, layouts and configurations of the microfluidic devices according to aspects of the present disclosure include varying geometries of the discrete features within the microfluidic devices. FIG. 6B is a schematic diagram showing a partial front view or top view of the microfluidic device 600 of FIG.6A, with a cross-section view along the line 6B-6B in FIG. 6A. Relative to the microfluidic device 100 discussed above, the microfluidic device 600 includes several additional variations.

In particular, the width of the main channel system 604 can vary between microfluidic devices. Such variation between microfluidic devices can occur through the entire main channel system 604, within only the central portion 612 of the main channel system 604, or throughout the main channel system 604 except for the central portion 612. For example, the width of the main channel system 604 of the microfluidic device 600 is reduced as compared to the microfluidic device 100. A reduction or enlargement of the width of the main channel system 604 can alter the dynamics of flow within the microfluidic device 600 to aid in distributing the biological specimens 628 within the chambers 614.

In addition, or in the alternative, to altering the width of the main channel system, the depth, cross-sectional profile, etc. of the main channel system of a microfluidic device according to aspects of the present disclosure can be altered to control the dynamics of flow within the main channel system.

The geometry of the channel openings of microfluidic devices also can vary to aid in distributing the biological specimens throughout the chambers. As shown in the inset of FIG. 1, the corners of the channel openings 118 can be substantially 90 degrees or square. Alternatively, as shown in FIG. 6B, the corners of the channel openings 618 can be rounded, as opposed to square. Moreover, the radius of curvature of the corners of the channel openings 618 can vary, such as having a large radius of curvature at all of the channel openings 618, or a small radius of curvature at all of the channel openings 618. In some aspects, the radius of curvature of the corners at the channel openings 618 can vary depending on the distance the channel openings 618 are from the inlet 608. For example, the radius of curvature of the corners at the channel openings 618 can become progressively larger or smaller as the distance the channel opening 618 are from the inlet 604 increases or decreases. Further, the corners at the channel openings 618 for each channel segment (in the case of multiple channel segments, e.g., 112-1 and 112-2) can be the same radius of curvature, or can be varying radii of curvature. Larger, smaller and varying radii of curvature of the corners at the channel openings 618 can aid in evenly distributing the biological specimens 628 among the chambers 614.

The geometry within the chambers of microfluidic devices also can vary to aid in retaining the biological specimens therein. As shown in the inset of FIG. 1, the profiles of the chambers 114 at the medium openings 120 can be substantially half circles to reduce the width of the chambers 114 at the interface with the medium openings 120. Alternatively, as shown in FIG. 6B, the chambers 614 at the medium openings 620 can include tapered portions 630. The tapered portions 630 can aid in capturing and retaining the biological specimens 628 within the chambers 614. The amount of taper can vary depending on the size of the biological specimen 628, the width of the chambers 614 relative to the width of the connecting channels 624, etc. Further, the taper of the tapered portions 630 shown in FIG. 6B is with respect to the width of the chambers 614. Alternatively, or in addition, the taper can be with respect to the height of the chambers 614. The taper of the tapered portions 630 can be linear, as shown in FIG. 6B. Alternatively, the taper of the tapered portions 630 can be curved, such as convex or concave, although not necessarily circular as shown in FIG. 1.

In some aspects, whether the chambers 614 include the tapered portions 630 can depend on the distance a particular chamber 614 is from the inlet 608. For example, a chamber 614 includes or does not include the tapered portions 630 if the chamber 614 is near or far from the inlet 608, respectively, or vice versa.

As shown in the cross-section portion of FIG. 6B, the depths of the connecting channels 624 can be less than the depths of the chambers 614. The depth of each of the connecting channels 624 can vary depending of the desired flow rates of medium through the connecting channels 624 and to aid in retaining the biological specimens within the chambers 614, such as preventing the biological specimens from entering into and escaping through the connecting channels 624.

Exemplary Methods of Using the Microfluidic Devices and/or Ssytems Described Herein The microfluidic devices and/or systems described herein offer a number of advantages. For example, it can enable high-throughput separation of a large number of target biological specimens into individual compartments and/or chambers. As discussed above, the design of the microfluidic devices also allows for providing fresh culture medium to each target biological specimen in its respective chamber without cross-talk or cross-contamination. Thus, one can design an experiment to test a number of different test conditions in the same microfluidic device. Since the culture medium and target biological specimens are contained in a sealed device and/or system, it can also offer containment of toxic compounds, pathogens, and/or other hazardous materials introduced into the microfluidic device for testing. Further, the microfluidic devices and/or systems described herein allow for automated fluid handling and real-time analytical capability for a wide range of assays, including, e.g., but not limited to live/dead assays, bioelectrical state, and organ volumes/morphologies. In addition, the microfluidic devices and/or systems described herein allows for recovering the target biological specimens from their respective chambers for further analysis and/or culture. Accordingly, the microfluidic devices and/or systems described herein can be used for various cell-based culture and/or assay applications and methods of using the same are provided herein.

In one aspect, a high throughput method of trapping single biological specimens is provided herein. The method comprises: (a) providing at least one or more microfluidic devices described herein with the channel openings being located below the corresponding channel segment in the direction of gravity; (b) introducing a fluid comprising target biological specimens into the inlet of the main channel system; (c) causing the fluid to flow across the central portion in a first direction from the inlet to the outlet; and (d) allowing at least a portion of the biological specimens to individually enter into the chambers.

To cause the fluid comprising target biological specimens to flow across the central portion from the inlet to the outlet, the central portion of the main channel system and the connecting channels are pre-filled with a fluid, e.g., as shown in FIG. 3A. Either a pressure-driven or a vacuum-driven approach can then be employed to load target biological specimens for trapping as shown in FIG. 3B. For example, pressure can be applied to an inlet 108 of the microfluidic device 100 for loading a fluid comprising the target biological specimens. This can cause the fluid to flow through medium opening 120 into the connecting channels 124 as well as the distribution segments 116-$n$. Due to the fluid flow, the target biological specimens (e.g., embryos) in the fluid will enter individual chambers that have not yet received a single biological specimen. For the chambers that have already received a single biological specimen, the fluid flow is blocked by the lodged biological specimen, and thus it is unlikely that another biological specimen will enter the occupied chambers. As a result, the target biological specimens are forced to travel farther downstream to available chambers. Similarly, vacuum can be used to load the target biological specimens into individual chambers. For example, upon introducing the target biological specimens through the inlet 108 of the main channel system 104, vacuum can be applied primarily to the medium inlet 122, with the main channel system 104 being closed. This creates the same effect as the pressure-driven loading approach. After loading the target biological specimens into individual chambers, the central portion 112 of the main channel system 104 can be flushed to remove any untrapped target biological specimens. The term "untrapped" as used herein refers to a target biological specimen that flows through the central portion 112 from the inlet 108 and the outlet 110 without entering into any chamber 114. While FIGS. 3A-3B illustrates loading and trapping of target biological specimens in one particular fluid flow direction, a reverse fluid flow can also be applied. In this embodiment, the inlet 108 of the main channel system 104 can serve as an outlet for exit of excess target biological specimens, while the outlet 110 of the main channel system can serve as an inlet for introduction of the target biological specimens.

The method can be used to trap or separate any target biological specimens into individual chambers. Non-limiting examples of the biological specimens include, but are not limited to, *Xenopus* organisms or embryos thereof, zebrafish organisms or embryos thereof, *C. elegans* organisms or embryos thereof, planaria organisms or embryos thereof, *Daphnia* organisms or embryos thereof, shrimp or embryos thereof, *Drosophila* organisms or embryos thereof, a tissue biopsy, an organoid, a cell, a cell cluster, and genetic variants thereof. In some embodiments, the method can be used to trap or separate spherical, aquatic target biological specimens (including, e.g., embryos of *Xenopus*, zebrafish, *C. elegans*, planaria, *Daphnia*, or shrimps) into individual chambers. For aquatic target biological specimens (including, e.g., embryos of *Xenopus*, zebrafish, *C. elegans*, planaria, *Daphnia*, or shrimps), the target biological specimens can be suspended in an aqueous fluid for loading and flowing through the main channel system. For non-aquatic target biological specimens (including, e.g., embryos of *Drosophila* or non-aquatic organisms), the target biological specimens can be suspended in a temporary fluid or an inert oil (e.g., a fluorinated oil) to enable trapping or separation of the target biological specimens into individual chambers. The temporary fluid or an inert oil can then be removed upon trapping or separation, and the target biological specimens disposed in the chambers can be cultured with periodic feeding or compound dosing via liquid injection through the corresponding medium opening of the corresponding chambers via the connecting channels.

For loading and/or trapping embryos, flow rates can vary depending, for example, on the dimensions of the chambers, channel segments, and/or connecting channels. For example, in some embodiments, a flow rate does not exceed 1-10 dyne/cm$^2$ to avoid cell/tissue/organism damage, and a lower shear rate is preferable. Flow rates that are significantly lower than that would not affect the cell/tissue/organism but can lead to a delay in dosing, which may need to be timed accurately in some applications (e.g., drug dosing for kinetic assays), or a delay in establishing culture conditions, which can lead to decreased viability or side effects.

After the target biological specimens are separated into individual chambers, they can be cultured independently. For example, when the target biological specimens are embryos, e.g., of small organisms such as *Xenopus* or zebrafish, they can be cultured in the chambers to grow over a period of time. Accordingly, in some embodiments, the method can further comprise, after trapping the single biological specimens into the chambers, causing culture medium to enter the chambers through the connecting channels, thereby providing nutrients to the biological specimens via the corresponding medium openings. For example, a culture medium (with or without a test agent or molecule) can be delivered to the chambers through the connecting channels by a pump system known in the art or as described herein such as a pressure-driven system or a vacuum-driven system.

In some embodiments, as shown in FIG. 3C, the method can further comprise causing a fluid to flow across the main channel via the central portion. This fluid flow can be used to remove or collect a sample (e.g., a fluid that has contacted the target biological specimens) from the chambers or secretion, cellular components and/or waste produced or derived from the biological specimens present in the chambers. In particular, the fluid can be flown in a direction reverse to the first direction in which the fluid flowed to separate the target biological specimens into individual chambers, e.g., using a pump system known in the art or described herein such as a pressure-driven system or a vacuum-driven system. This approach can enable the target biological specimens in their individual chambers to experience only culture medium introduced through the medium opening of the respective chambers, instead of "exposed" fluid from the main channel that has contacted other target biological specimens. Thus, the reversal flow can minimize exposure of the trapped biological specimens to an "exposed" fluid that have been in contact with other trapped biological specimens. In addition, reversing the flow can allow for a single inlet to receive a fresh culture medium, while the "exposed" fluid can be removed and flushed out through the inlet 108 of the main channel system 104, where the inlet 108 can serve as both an inlet for introduction of biological specimens, and an outlet for exit of the "exposed" fluid.

Similar approach can be used to collect a fluid sample from the chambers having individual target biological specimens. In some embodiments, the cellular components (e.g., DNA, RNA, and/or protein) can be derived from the target biological specimens (e.g., embryos or cells or tissues) present in the chambers by contacting the target biological specimens with a lysis agent prior to flowing a fluid across the main channel in a reversed direction to collect a sample. The fluid sample can comprise conditioned culture medium, and/or secreted molecules and/or biological molecules (e.g., nucleic acid molecules, protein molecules) derived from the biological specimens.

In some embodiments, the target biological specimens in the chambers can be contacted with a test agent. Accordingly, another aspect provided herein relates to a method of determining an effect of one or a plurality of test agents on single biological specimens. Such method comprises: (a) providing at least one or more microfluidic devices described herein with the channel openings being located below the corresponding channel segment in the direction of gravity; (b) introducing a fluid comprising target biological specimens into the inlet of the main channel system; (c) causing the fluid to flow across the central portion; (d) allowing at least a portion of the biological specimens to individually enter into the chambers, thereby trapping single biological specimens in the chambers; (e) causing culture medium comprising at least one test agent to enter the chambers through the connecting channels, thereby exposing the biological specimens to the test agent via the medium openings of the corresponding chambers; and (f) detecting response of the biological specimens and/or assaying a sample from the chambers containing the biological specimens. Thus, an effect of the test agent(s) on the biological specimens can be determined.

Before contacting the target biological specimens with a test agent, the target biological specimens are separated into the individual chambers using one or more embodiments of the method of trapping single biological specimens as described above, e.g., as shown in FIGS. 3A-3B. The culture medium comprising at least one test agent can then be introduced into the chambers through the connecting channels, e.g., by a pump system known in the art or described herein such as a pressure-driven system or a vacuum-driven system. For example, when a vacuum-driven or a vacuum actuation system is used for loading target biological specimens into the chambers, vacuum (or a downstream pump) can be primarily applied to an on-device reservoir 109 and the outlet 110 of the main channel system 104 can be suctioned out only after the chambers 114 are loaded. Other work flows known to one skill in the art can also be used. For example, when a pressure-driven system is used, pressure can be applied to an on-device reservoir 109. In either embodiments (e.g., vacuum and pressure), either the outlet 110 of the main channel system 104 or the inlet 108 of the main channel system 104 can be sealed to avoid fluid flow in both directions for simplicity.

As discussed above, in some embodiments, as shown in FIG. 3C, the method can further comprise causing a fluid to flow across the main channel via the central portion, e.g., to remove a sample (e.g., a fluid that has contacted the target biological specimens) from the chambers or secretion and/or waste produced from the biological specimens present in the chambers. In particular, the fluid can be flown in a direction reverse to the first direction in which the fluid flowed to separate the target biological specimens into individual chambers, e.g., using a pump system known in the art or described herein such as a pressure-driven system or a vacuum-driven system. For example, when a vacuum-driven system is used for culture, vacuum can be applied to the inlet 108 of the main channel system 104.

As discussed above, since the culture medium and the target biological specimens are contained in a sealed device or system, any test agent, whether it is infectious, toxic, or pathogenic, can be tested using the microfluidic devices and/or systems described herein. Examples of a test agent include, but are not limited to proteins, peptides, nucleic acids, antigens, nanoparticles, environmental toxins or pollutants, carcinogens, small molecules, drugs or drug candidates, vaccine or vaccine candidates, pro-inflammatory agents, viruses, bacteria, unicellular organisms, cytokines, infectious agents, gene expression-modifying agents (e.g., morpholinos, siRNAs, CRISPR), and any combinations thereof.

Depending on the objective of an experiment, various analytical methods and/or assays can be performed to detect response of the biological specimens and/or to analyze a sample derived from the biological specimens of the chambers. Non-limiting examples of such analytical methods and/or assays include cell labeling, immunostaining, optical or microscopic imaging (e.g., immunofluorescence microscopy and/or scanning electron microscopy), gene expression analysis, cytokine/chemokine secretion analysis, metabolite analysis, polymerase chain reaction, immunoassays, ELISA, gene arrays, pathogen quantification, and any combinations thereof. For example, in one embodiment where the method described herein is designed to screen for teratogenic or anti-angiogenic activity of test agents such as chemicals or potential environmental toxins, imaging analysis of embryos that have been exposed to those test agents for detection of malformed embryos, inhibition in cell differentiation and/or inhibition in angiogenesis can be performed.

The biological specimens can be assayed in situ within the respective chambers or can be recovered from the respective chambers for analysis. In some embodiments, the biological specimens can be recovered or removed from the respective chambers by creating an aperture in the optically transparent cover over the chambers. In some embodiments, the biological specimens can be recovered or removed from the respective chambers by flowing a fluid through the corresponding connecting channels at a high flow rate such that the biological specimens can be forced out of the respective chambers. This is essentially reversing the process of loading the target biological specimens into the individual chambers. This approach to recover or remove the target biological specimens from the respective chambers can be useful if a population of the target biological specimens are desired to be recovered quickly and pooled together into the same group (e.g., in the case of the target biological specimen duplicates treated with the same dose of a test agent or molecule).

In some embodiments, at least a subset of the biological specimens present in their individual chambers can be exposed to an agent known to induce a disease-specific phenotype. Thus, each of those biological specimens develops into an individual disease model, e.g., for study of the disease, or for identification of a treatment. In these embodiments, the method can further comprise exposing the biological specimens, upon exposure to a disease-inducing agent, to a library of drug candidates in order to screen for a drug candidate that treats the disease-specific phenotype. Without limitations, the method described herein can be used to screened for tumor suppressors, regenerative repair inducers, compounds that counteract birth defects (e.g., induced by genetics and/or specific toxins), or compounds that modulate morphogenesis (e.g., for use in regenerative medicine), when the target biological specimens (e.g., embryos such as *Xenopus* embryos) are pre-exposed to an appropriate disease-inducing agent to induce a desirable disease-specific phenotype. For example, in one embodiment, the biological specimens pre-exposed to a known toxin or carcinogen can be exposed to a library of drug candidate to screen for an agent that reverses or reduces an effect of the known toxin or carcinogen on the biological specimens.

Accordingly, not only can the microfluidic devices, systems and/or methods described herein be used to screen compounds or agents for negative effects (e.g., for being toxins or carcinogens), but they can also be used to screen compounds or agents for "amelioration" or rescue of a known agent with a negative effect (e.g., a toxin or carcinogen).

Similarly, the biological specimens can be pre-exposed to an infectious agent, and then be contacted with a library of drug candidates to screen for tolerance, susceptibility or resistance to the infectious agent. By way of example only, a single microfluidic device described herein can be configured to test at least 8 or more (including, e.g., at least 10, at least 15, at least 20 or more) test agents or drug candidates with approximately 5-20 (e.g., about 10) target biological specimens (e.g., embryos) for each different condition. The target biological specimens (e.g., embryos) can be first contacted with microbes (e.g., bacteria) or infectious agents (e.g., viruses), followed by exposure to a desired test agent or drug candidate. In some embodiments, the microbes (e.g., bacteria) or infectious agents (e.g., viruses) can be labeled with a detectable label. Accordingly, in one embodiment, up to 4-color epifluorescence and brightfield imaging of single biological specimens (e.g., embryos) and fluorescent protein-expressing microbes (e.g., bacteria) or infectious agents (e.g., virus) can be integrated to provide a real-time analytical capability for a wide range of assays, including, e.g., but not limited to live/dead assays, bioelectrical state, organ volumes, and/or morphologies, etc. The system can be controlled by a user-friendly web application that can provide remote control of the system and experimental design. Output images can be integrated with image processing software for automated analysis of response of the biological specimens (e.g., embryos) to microbes (e.g., bacteria) or infectious agents (e.g., viruses). Specific target biological specimens (e.g., embryos) can be recovered for downstream analysis using the method described herein (e.g., by pipette to break through the gas-permeable sealing membrane, or by flowing a fluid through the connecting channels at a high flow rate to force the target biological specimens out of the chambers). Such system and method described herein can facilitate high-throughput setup and operation by relying on, e.g., robotic and automated fluid handling, such as vacuum fluid handling, and epifluorescence imaging, in conjunction with the microfluidic device design described herein that enables rapid separation of the target biological specimens (e.g., embryos) into the individual chambers and alignment for imaging and containment of pathogens and infected waste streams.

As discussed above, one of the advantages of the microfluidic devices and/or systems described herein is that target biological specimens can be separated into individual chambers. Thus, the diversity of a population of target biological specimens can be maintained by preventing rare biological specimens being outcompeted by dominant or fast-growing or high abundance target biological specimens. As such, rare biological specimens can be identified and methods of achieving such purpose are also described herein. The method described herein can also be used to enrich a sample with rare biological specimens. The term "rare biological specimen" refers to a biological specimen (e.g., a cell or a cluster of cells, or an embryo) that is not frequently present in a fluid sample, e.g., a biological fluid sample. For example, a rare biological specimen can be a biological specimen having distinct gene signature(s), mutation(s), transcriptome, and/or polymorphisms. In some embodiments, a rare biological specimen can be a diseased specimen (e.g., a cell or an embryo). In some embodiments, a rare biological specimen can be a biological specimen present in a sample with a frequency several orders of magnitude (e.g., at least about 100-fold, at least about 1000-fold, at least about 10000-fold) less than other abundant biological specimens typically present in the sample. In some embodiments, the rare biological specimen can be a rare cell found infrequently in circulating blood, e.g., less than 100 cells (including less than 10 cells, less than 1 cell) per $10^8$ mononuclear cells in about 50 mL of peripheral blood. In some embodiments, a rare cell can be a normal cell or a diseased cell. Examples of rare cells include, but are not limited to, circulating tumor cells, progenitor cells, e.g., collected for bone marrow transplantation, blood vessel-forming progenitor cells, stem cells, circulating fetal cells, e.g., in maternal peripheral blood for prenatal diagnosis, virally-infected cells, cell subsets collected and manipulated for cell and gene therapy, and cell subpopulations purified for subsequent gene expression or proteomic analysis, other cells related to disease progression, and any combinations thereof. In some embodiments, the presence of the rare biological specimen can be present as an indicator of an abnormal condition, such as infectious disease, chronic disease, injury, proliferative diseases, or pregnancy. Accordingly, in some embodiments, the microfluidic devices and/or systems described herein can be used to detect and/or identify a rare biological specimen from a sample.

In one aspect, the method of identifying a rare biological specimen from a sample comprises: (a) providing at least one or more microfluidic devices described herein with the channel openings being located below the corresponding channel segment in the direction of gravity; (b) introducing a sample comprising biological specimens to be assayed into the inlet of the main channel system; (c) causing the fluid to flow across the central portion; (d) allowing the biological specimens to individually enter into the chambers, thereby separating single biological specimens into the chambers; and (e) assaying the biological specimens in the chambers and/or assaying an aliquot of culture medium from the chambers containing the biological specimens, thereby identifying a rare biological specimen from the sample.

As described above, the target biological specimens are separated into the individual chambers using one or more embodiments of the method of trapping single biological specimens as described above, e.g., as shown in FIGS. 3A-3B. A fluid comprising a culture medium can then be introduced into the chambers through the connecting channels, e.g., by a pump system known in the art or described herein such as a pressure-driven system or a vacuum-driven system. As discussed above, in some embodiments, as shown in FIG. 3C, the method can further comprise causing a fluid to flow across the main channel via the central portion, e.g., to remove a sample (e.g., a fluid that has contacted the target biological specimens) from the chambers or secretion and/or waste produced from the biological specimens present in the chambers. In particular, the fluid can be flown in a direction reverse to the first direction in which the fluid flowed to separate the target biological specimens into individual chambers, e.g., using a pump system known in the art or described herein such as a pressure-driven system or a vacuum-driven system.

To identify a rare biological specimen, different cell and/or molecular assays can be performed to analyze behavior of the biological specimens and/or molecules secreted by the biological specimens, including, e.g., but not limited to cell labeling, immunostaining, optical or microscopic imaging (e.g., immunofluorescence microscopy and/or scanning electron microscopy), gene expression analysis, cytokine/chemokine secretion analysis, metabolite analysis, polymerase chain reaction, immunoassays, ELISA, gene arrays, or any combinations thereof.

The rare biological specimens can be assayed in situ within the respective chambers or can be recovered from the respective chambers for downstream analysis and/or culture. For example, the biological specimens can be recovered or removed from the respective chambers by creating an aperture in the optically transparent cover over the chambers. The isolated, rare biological specimen(s) can be subjected to a whole genome sequencing, e.g., to search for the genetic basis (e.g., distinct mutations or polymorphisms) of any response, and/or to cell culture for growing the identified rare biological specimen to a larger population.

In some embodiments, identified rare individual embryos (e.g., but not limited to *Xenopus*, zebrafish, dropsophila, *C. elegans*) can be grown to maturity to breed genetic responder populations for further study.

In some embodiments, the microfluidic devices and/or systems described herein can be used to grow stem cell organoids and identify appropriate stem cell organoids for various clinical applications. As used herein, the term "stem cell organoid" refers to a three-dimensional cellular structure generated from stem cells in vitro. The stem cell organoids are grown to mimic organ structure and/or function. Typically, an organoid is a cluster of tens to hundreds of cells.

In one aspect, a method of growing a stem cell organoid comprises: (a) providing at least one or more microfluidic devices described herein with the channel openings being located below the corresponding channel segment in the direction of gravity; (b) introducing a sample comprising stem cells into the inlet of the main channel system; (c) causing the fluid to flow across the central portion; (d) allowing at least one or more stem cells to enter into the chambers, thereby trapping at least one or more stem cells in the chambers; and (e) culturing the stem cells in the respective chambers for a period of time such that the stem cells differentiate and form an organoid.

The microfluidic devices described herein can be scaled down for single stem cell capture and culture. If single cell culture is desired, single cells can be captured by using a small chamber volume and flowing in a dilute cell suspension. Alternatively, larger chamber volume and/or more concentrated cell suspension can be used to facilitate capture of multiple stem cells in a single chamber. For example, multiple stem cells (e.g., at least two or more, including, e.g., at least three, at least four, at least five or more) can be captured in a single chamber to explore interaction between them.

Exemplary stem cells that can be used in the method described herein include, but are not limited to bone marrow-derived stem cells and/or hematopoietic stem cells. In some embodiments, stem cells can also include embryonic stem (ES) cells, ES- derived cells, induced pluripotent stem cells, adult stem cells, and stem cell progenitors, including, without limitation, hematopoietic, neural, stromal, muscle, cardiovascular, hepatic, pulmonary, and gastrointestinal stem cells.

The stem cells can be separated into the individual chambers using one or more embodiments of the method of trapping single biological specimens as described above, e.g., as shown in FIGS. 3A-3B. A fluid comprising a culture medium and/or a cell differentiation medium can then be introduced into the chambers through the connecting channels, e.g., by a pump system known in the art or described herein such as a pressure-driven system or a vacuum-driven system. As discussed above, in some embodiments, as shown in FIG. 3C, the method can further comprise causing a fluid to flow across the main channel via the central portion, e.g., to remove a sample (e.g., a fluid that has contacted the target biological specimens) from the chambers or secretion and/or waste produced from the stem cells and/or resulting organoid present in the chambers. In particular, the fluid can be flown in a direction reverse to the first direction in which the fluid flowed to separate the target the stem cells into individual chambers, e.g., using a pump system known in the art or described herein such as a pressure-driven system or a vacuum-driven system.

To identify a stem cell organoid for a target application, the method can further comprise assaying the organoid in the respective chambers and/or assaying an aliquot of culture medium from the chambers containing the organoid using any art-recognized cell and/or molecular assays. Different cell and/or molecular assays can be performed to assay an organoid and/or a sample derived from an organoid, including, e.g., but not limited to cell labeling, immunostaining, optical or microscopic imaging (e.g., immunofluorescence microscopy and/or scanning electron microscopy), gene expression analysis, cytokine/chemokine secretion analysis, metabolite analysis, polymerase chain reaction, immunoassays, ELISA, gene arrays, or any combinations thereof.

The stem cell organoids can be assayed in situ within the respective chambers or they can be recovered from the respective chambers for downstream analysis and/or application. In some embodiments, the stem cell organoid can be recovered or removed from the respective chambers by creating an aperture in the optically transparent cover over the chambers.

Fluid Samples and Target Biological Species

As used herein, the term "fluid sample" or "sample" or "fluid" refers to any flowable material comprising one or more target molecules. In some embodiments where a fluid sample is introduced into the microfluidic devices and/or systems described herein for single cell purpose, the target molecules included in the fluid sample can comprise target biological species. As used herein, the term "target biological specimen" refers to a single cell, a cluster of cells, a multicellular tissue structure, a 3D tissue, or an embryo, or genetic variants thereof. In some embodiments, the target biological specimen can be genetically altered (e.g., with morpholios, siRNA, CRISPR and/or other gene-editing agents) or mutated to increase range of variation. Examples of target biological specimens include, but are not limited to *Xenopus* or embryos thereof, zebrafish or embryos thereof, *C. elegans* or embryos thereof, planaria or embryos thereof, *Daphnia* or embryos thereof, shrimp or embryos thereof, *Drosophila* or embryos thereof, 3D tissue cultures, tissue biopsy, organoids such as tissue organoids or stem cell organoids, cells, cell clusters, and other non-embryo living mateirals. Without wishing to be bound by theory, the fluid samples can be liquid (e.g., aqueous or non-aqueous), supercritical fluid, gases, solutions, and suspensions.

In some embodiments where a fluid sample that has been contacted with the target biological specimens is being removed from the chamber, e.g., for further analysis, the fluid sample can comprise secreted molecules, cytokines and/or wastes from the target biological specimen cultured in the respective chamber.

In some embodiments where a fluid is introduced into the target biological specimen(s) disposed in the chambers, the fluid can comprise a cell culture medium with or without a test agent or molecule.

In some embodiments, the fluid sample or fluid can include untreated or pre-treated (or pre-processed) biological fluid sample or fluid. The term "biological fluid sample" or "biological fluid" as used herein refers to aqueous fluids of biological origin, including solutions, suspensions, dispersions, and gels, and thus can or cannot contain undissolved particulate matter. Exemplary biological fluid samples include, but are not limited to, blood (including whole blood, plasma, cord blood and serum), lactation products (e.g., milk), amniotic fluids, sputum, saliva, urine, semen, cerebrospinal fluid, bronchial aspirate, perspiration, mucus, liquefied feces, synovial fluid, lymphatic fluid, tears, tracheal aspirate, and fractions thereof. In some embodiments, the biological fluid sample can be a whole blood sample or a fraction thereof. In some embodiments, the biological fluid sample can include a subject's tissue extract, e.g., a homogenized tissue extract.

In some embodiments, the biological fluid sample obtained from a subject, e.g., a mammalian subject such as a human subject or a domestic pet such as a cat or a dog, can contain cells from the subject. In other embodiments, the biological fluid sample can contain non-cellular biological material, such as non-cellular fractions of blood, saliva, or urine, that can be used to measure plasma/serum biomarker expression levels.

The biological fluid sample can be freshly collected from a subject or a previously collected sample. In some embodiments, the biological fluid sample or fluid sample can be a frozen sample, e.g., a frozen tissue or fluid sample such as urine, blood, serum or plasma. The frozen sample can be thawed before employing the microfluidic devices, kits and/or methods described herein.

In some embodiments, the biological fluid sample or any fluid sample described herein can be treated with a chemical and/or biological reagent prior to use with the microfluidic devices and/or methods described herein. In some embodiments, at least one of the chemical and/or biological reagents can be present in the sample container before a fluid sample is added to the sample container. For example, blood can be collected into a blood collection tube such as VACUTAINER®, which has already contained heparin. Examples of the chemical and/or biological reagents can include, without limitations, surfactants and detergents, salts, cell lysing reagents, anticoagulants, degradative enzymes (e.g., proteases, lipases, nucleases, collagenases, cellulases, amylases), and solvents such as buffer solutions.

The skilled artisan is well aware of methods and processes appropriate for pre-processing of the fluid sample or the biological fluid sample, e.g., blood, if any, required for separating one or more target biological specimens, e.g., rare cells, therefrom. For example, reagents and treatments for processing blood before assaying are well known in the art, e.g., as used for assays on Abbott TDx, AxSYM®, and ARCHITECT® analyzers (Abbott Laboratories), as described in the literature (see, e.g., Yatscoff et al., Abbott TDx Monoclonal Antibody Assay Evaluated for Measuring Cyclosporine in Whole Blood, Clin. Chem. 36: 1969-1973 (1990), and Wallemacq et al., Evaluation of the New AxSYM Cyclosporine Assay: Comparison with TDx Monoclonal Whole Blood and EMIT Cyclosporine Assays, Clin. Chem. 45: 432-435 (1999)), and/or as commercially available. Additionally, pretreatment can be done as described in Abbott's U.S. Pat. No. 5,135,875, European Pat. Pub. No. 0 471 293, U.S. Pat. No. 7,993,851, U.S. Pat. App. Pub. No. 2008/0020401, U.S. Pat. App. Pub. No. 2011/0294140, and U.S. Pat. App. Pub. No. 2012/0288875, content of all of which is incorporated herein by reference. It is to be understood that one or more of these known reagents and/or treatments can be used in addition to or alternatively to the sample treatment described herein.

In some embodiments, after lysis of red blood cells, the treated blood sample can be subjected to a mechanical force, e.g., centrifugation, to collect the remaining nucleated cells in the blood sample. The collected nucleated cells can then be resuspended in a biocompatible buffer solution, e.g., PBS. The biocompatible buffer solution can include at least one agent, e.g., a blocking agent, e.g., bovine serum albumin, and an anticoagulant, e.g., EDTA. In some embodiments, a fluid sample or a biological fluid sample can be a whole blood sample already treated with a red blood cell lysis buffer.

Other than biological fluid samples obtained from a subject, such as a mammalian subject, e.g., a human subject and/or a domesticated pet, e.g., a cat or a dog, additional examples of biological fluid samples can include cell culture fluids, including those obtained by culturing, for example, of single- or multi-cell organisms, including prokaryotes (e.g., bacteria) and eukaryotes (e.g., animal cells, plant cells, yeasts, fungi), or embryos, and including fractions thereof.

In some embodiments, the cell culture fluids can include culture media and/or reagents comprising biological products (e.g., proteins secreted by cells cultured therein).

As used herein, the term "cell culture medium" refers to a medium for maintaining a tissue or cell population, or culturing a cell population containing nutrients that maintain cell viability and support proliferation. The cell culture medium can contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art. The media can include media to which cells have been already been added, i.e., media obtained from ongoing cell culture experiments, or in other embodiments, be media prior to the addition of cells.

As used herein, the term "reagent" refers to any solution used in a laboratory or clinical setting for biomedical and molecular biology applications. Reagents include, but are not limited to, saline solutions, PBS solutions, buffer solutions, such as phosphate buffers, EDTA, Tris solutions, and the like. Reagent solutions can be used to create other reagent solutions. For example, Tris solutions and EDTA solutions are combined in specific ratios to create "TE" reagents for use in molecular biology applications.

Without wishing to be bound, in some embodiments, the fluid sample or fluid to be used with the microfluidic devices and/or methods described herein can be a non-biological fluid. As used herein, the term "non-biological fluid" refers to any aqueous, non-aqueous or gaseous sample that is not a biological fluid as the term is defined herein. Exemplary non-biological fluids include, but are not limited to, water, salt water, brine, organic solvents such as alcohols (e.g., methanol, ethanol, isopropyl alcohol, and butanol), saline solutions, sugar solutions, carbohydrate solutions, lipid solutions, nucleic acid solutions, hydrocarbons (e.g. liquid hydrocarbons), acids, gasolines, petroleum, liquefied samples (e.g., liquefied foods), gases (e.g., oxygen, $CO_2$, air, nitrogen, or an inert gas), and mixtures thereof.

Exemplary Methods to Fabricate the Microfluidic Devices Described Herein

Any embodiments of the devices described herein can be made of any material that is compatible with a fluid. In some embodiments, the material for fabrication of the devices described herein can be substantially transparent so that they can be viewed under a microscope, e.g., for in situ analysis of the target biological specimens present in the chambers. Exemplary materials that can be used to fabricate different embodiments of the microfluidic devices described herein can include, but are not limited to, glass, co-polymer, polymer or any combinations thereof. Exemplary polymers include, but are not limited to, polyurethanes, rubber, molded plastic, polymethylmethacrylate (PMMA), polycarbonate, polytetrafluoroethylene (TEFLON™), polyvinylchloride (PVC), polydimethylsiloxane (PDMS), and polysulfone. The ether-based, aliphatic polyurethane described in the International Application Publication No. WO/2012/154729, the content of which is incorporated herein by reference, can also be used to fabricate the devices described herein.

The methods used in fabrication of any embodiments of the microfluidic devices described herein can vary with the materials used, and include embossing, soft lithography methods, microassembly, bulk micromachining methods, surface micro-machining methods, standard lithographic methods, wet etching, reactive ion etching, plasma etching, laser etching, stereolithography and laser chemical three-dimensional writing methods, solid-object printing, machining, modular assembly methods, replica molding methods, injection molding methods, hot molding methods, laser ablation methods, combinations of methods, and other methods known in the art. A variety of exemplary fabrication methods are described in Fiorini and Chiu, 2005, "Disposable microfluidic devices: fabrication, function, and application" Biotechniques 38:429-446; Beebe et al., 2000, "Microfluidic tectonics: a comprehensive construction platform for microfluidic systems." Proc. Natl. Acad. Sci. USA 97:13488-13493; Rossier et al., 2002, "Plasma etched polymer microelectrochemical systems" Lab Chip 2:145-150; Becker et al., 2002, "Polymer microfluidic devices" Talanta 56:267-287; Becker et al., 2000, "Polymer microfabrication methods for microfluidic analytical applications" Electrophoresis 21:12-26; U.S. Pat. No. 6,767,706 B2, e.g., Section 6.8 "Microfabrication of a Silicon Device"; McDonald et al., 2002, "Poly(dimethylsiloxane) as a material for fabricating microfluidic devices" Accounts of Chemical Research 35: 491-499. Piccin et al., 2007, "Polyurethane from biosource as a new material for fabrication of microfluidic devices by rapid prototyping" Journal of Chromatography A 1173: 151-158. Each of these references is incorporated herein by reference.

In some embodiments, the microfluidic devices described herein can be formed by replica molding, for example, in which a replica of the selected material conforms to the shape of a master or a mold and replicates the features of the master or the mold. In some embodiments, the replica can be further sealed to a surface to enclose at least one fluidic element.

In some embodiments, the microfluidic devices described herein can be formed by machining or micromachining. The term "micromachining" as used herein can encompass bulk micromachining or surface micromachining as recognized in the art. In one embodiment, bulk micromachining defines microstructures such as fluidic elements by selectively etching inside a substrate. In one embodiment, surface micromachining creates microstructures such as fluidic elements on top of a substrate material.

In some embodiments, the microfluidic devices described herein can be formed by solid-object printing. In some embodiments, the solid-object printing can take a three-dimensional (3D) computer-aided design file to make a series of cross-sectional slices. Each slice can then be printed on top of one another to create the 3D solid object.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein the term "comprising" or "comprises" is used in reference to compositions, methods, and respective component(s) thereof, that are essential to the invention, yet open to the inclusion of unspecified elements, whether essential or not. Additionally, the term "comprising" or "comprises" includes "consisting essentially of" and "consisting of."

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, the terms "culture," "culturing" and "cell culture" generally refers to establishment and/or maintenance of cells in an in vitro environment. In some embodiments, cell culture can encompass cell passaging as described herein.

The term "passageway" as used herein generally refers to a channel, a conduit, a duct, or a pathway through and along which a fluid (e.g., gas or liquid) can flow, pass or move.

To the extent not already indicated, it will be understood by those of ordinary skill in the art that any one of the various embodiments herein described and illustrated may be further modified to incorporate features shown in any of the other embodiments disclosed herein.

It is understood that the foregoing detailed description and examples are illustrative only and are not to be taken as limitations upon the scope of the invention. Various changes and modifications to the disclosed embodiments, which will be apparent to those of skill in the art, may be made without departing from the spirit and scope of the present invention. Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A microfluidic device comprising:
   a main channel system having an inlet, an outlet, a central portion located between the inlet and the outlet, and a plurality of first chambers, the first chambers extending transversely to a first channel segment within the central portion, each of the first chambers having a channel opening that fluidly communicates with the first channel segment and a medium opening located away from the channel opening, each of the first chambers being sized to receive a single target biological specimen from the first channel segment, each of the first chambers being in an upright position and extending transversely only on a lower side of the first channel segment, the channel opening of each of the first chambers being located below the first channel segment in the direction of gravity; and a medium-manifold system having a medium inlet for receiving a culture medium and a plurality of first connecting channels, each of the first connecting channels distributing the culture medium to a corresponding first chamber of the plurality of first chambers through the medium opening of the corresponding first chamber, each of the first connecting channels being in fluid communication with the medium opening of the corresponding first chamber; and wherein each of the first connecting channels is configured such that the culture medium exposed to the biological specimen received in the corresponding first chamber does not contact another biological specimen received in another first chamber.

2. A microfluidic device comprising:

a main channel system having an inlet, an outlet, a central portion located between the inlet and the outlet, and a plurality of first chambers, the first chambers extending transversely to a first channel segment within the central portion, each of the first chambers having a channel opening that fluidly communicates with the first channel segment and a medium opening located away from the channel opening, each of the first chambers being in an upright position and extending transversely only on a lower side of the first channel segment, the channel opening of each of the first chambers being located below the first channel in the direction of gravity; and a medium-manifold system that includes a medium inlet for receiving a culture medium and a plurality of first connecting channels, each of the first connecting channels distributing the medium to a corresponding first chamber of the plurality of first chambers through the medium opening of the corresponding first chamber, each of the first connecting channels being in fluid communication with the medium opening of the corresponding first chamber;

wherein each of the first connecting channels is configured such that the culture medium exposed to the biological specimen received in the corresponding first chamber does not contact another biological specimen received in another first chamber; and wherein each of the first chambers is sized in a manner such that when the main channel system passes a seeding fluid containing a plurality of target biological specimens through the first channel segment, a first portion of the seeding fluid initially undergoes at a first flow rate through a first receiving chamber of the plurality of chambers and exits through the medium opening, and a second portion of the fluid undergoes at a second flow rate through the first receiving chamber after one of the target biological specimens becomes lodged with the first receiving chamber, wherein the second flow rate is substantially less than the first flow rate so as to reduce the likelihood of a second target biological specimen entering the first receiving chamber.

3. A microfluidic device comprising:

a main channel system having an inlet, an outlet, a central portion located between the inlet and the outlet, and a plurality of first chambers, the first chambers extending transversely to a first channel segment within the central portion, each of the first chambers having a channel opening that fluidly communicates with the first channel segment and a medium opening located away from the channel opening, each of the first chambers being in an upright position and extending transversely only on a lower side of the first channel segment, the channel opening of each of the first chambers being located below the first channel in the direction of gravity;

a medium-manifold system having a medium inlet for receiving a culture medium and a plurality of first connecting channels, each of the first connecting channels distributing the culture medium to a corresponding first chamber of the plurality of first chambers through the medium opening of the corresponding first chamber, each of the first connecting channels being in fluid communication with the medium opening of the corresponding first chamber; and wherein a seeding fluid comprising a plurality of target biological specimens flows from the inlet, through the first channel segment in a first direction to populate the first chambers with target biological specimens, to the outlet, and upon the first chambers being populated with target biological specimens, the culture medium flows past the target biological specimens in the first chambers toward the first channel segment and then within the first channel segment in a second direction that is opposite of the first direction.

4. The microfluidic device of claim 1, wherein the main channel system further comprises a plurality of second chambers, the plurality of second chambers extending transversely to a second channel segment within the central portion, each of the plurality of second chambers having a channel opening that fluidly communicates with the second channel segment and a medium opening located away from the channel opening; and the first channel segment and the second channel segment are fluidly connected.

5. The microfluidic device of claim 1, wherein the medium-manifold system further comprises a plurality of second connecting channels, wherein each of the second connecting channels distributes a culture medium to the corresponding second chamber through the second medium opening of the corresponding second chamber.

6. The microfluidic device of claim 1, wherein no connecting channels are configured to extend transversely from the central portion of the main channel system.

7. The microfluidic device of claim 1, wherein the central portion comprises a plurality of channel segments along a pre-determined path.

8. The microfluidic device of claim 1, further comprising a main body and an optically transparent cover, the main body and the optically transparent cover defining the main channel system and the medium-manifold system.

9. The microfluidic device of claim 8, wherein the optically transparent cover comprises a gas-permeable sealing membrane.

10. The microfluidic device of claim 1, wherein each of the chambers is sized to receive a single *Xenopus* embryo that will develop in response to exposure to an agent introduced by flow of the culture medium.

11. The microfluidic device of claim 10, wherein each of the chambers has a depth that is less than the anticipated size of the *Xenopus* embryo after growth over a fixed time period such that at least a portion of the grown *Xenopus* embryo remains within the chamber after the fixed time period.

12. The microfluidic device of claim 10, wherein each of the chambers has a depth that is longer than the anticipated size of the *Xenopus* embryo after growth over a fixed time period such that the grown *Xenopus* embryo remains entirely within the chamber after the fixed time period.

13. The microfluidic device of claim 1, wherein each of the chambers has a width substantially equivalent to the anticipated size of the Xenpus embryo after growth over a fixed time period such that the grown *Xenopus* embryo has its ventral side or dorsal side up and remains unchanged in the orientation after the fixed time period.

14. The microfluidic device of claim 10, wherein the cross-section of the chambers have a width of about 1.75 mm and a length of about 2.5 mm.

15. The microfluidic device of claim 10, wherein the chambers have a depth of about 8 mm.

16. A system comprising:
   a plurality of the microfluidic devices of claim 1;
   a plurality of holders, each of the plurality of holders configured to hold one or more of the plurality of the microfluidic; and
   a fluid handling module to control fluid flow in the main channel system and the medium-manifold system.

* * * * *